US009656029B2

(12) United States Patent
Tsang et al.

(10) Patent No.: US 9,656,029 B2
(45) Date of Patent: May 23, 2017

(54) PLURAL MEDICAL ITEM WARMING SYSTEM AND METHOD FOR WARMING A PLURALITY OF MEDICAL ITEMS TO DESIRED TEMPERATURES

(71) Applicant: Medical Solutions, Inc., Chantilly, VA (US)

(72) Inventors: Raymond Tsang, Ashburn, VA (US); Bruce Heymann, McLean, VA (US); Tarry Faries, McLean, VA (US)

(73) Assignee: Medical Solutions, Inc., Chantilly, VA (US)

( * ) Notice: Subject to any disclaimer, the term of this patent is extended or adjusted under 35 U.S.C. 154(b) by 283 days.

(21) Appl. No.: 14/178,408

(22) Filed: Feb. 12, 2014

(65) Prior Publication Data

US 2014/0231406 A1    Aug. 21, 2014

Related U.S. Application Data

(60) Provisional application No. 61/765,313, filed on Feb. 15, 2013.

(51) Int. Cl.
*A21B 1/00* (2006.01)
*A61M 5/00* (2006.01)
(Continued)

(52) U.S. Cl.
CPC ........ *A61M 5/44* (2013.01); *A61M 2205/3368* (2013.01); *A61M 2205/36* (2013.01); *A61M 2209/084* (2013.01)

(58) Field of Classification Search
CPC ...... A61M 2205/3368; A61M 2205/36; A61M 2209/084; A61M 5/44
(Continued)

(56) References Cited

U.S. PATENT DOCUMENTS 522,866 A    7/1894   Weinhagen et al.
558,979 A    4/1896   Noble
(Continued)

FOREIGN PATENT DOCUMENTS

DE    3742927 A1    7/1989
DE    19752578 A1   6/1999
(Continued)

OTHER PUBLICATIONS

Health Devices, vol. 25, No. 10, Oct. 1996.
(Continued)

*Primary Examiner* — Dana Ross
*Assistant Examiner* — Ket D Dang
(74) *Attorney, Agent, or Firm* — Edell, Shapiro & Finnan, LLC

(57) ABSTRACT

Present invention embodiments include a thermal treatment system for thermally treating and individually monitoring a plurality of medical or other items. The thermal treatment system includes a modular configuration with a control unit and one or more modular units coupled to the control unit, where each of the control and modular units thermally treat a plurality of corresponding medical items. The control unit includes a display to interact with a user for setting a desired temperature, and controls the modular units to thermally treat corresponding medical items to the desired temperature.

27 Claims, 11 Drawing Sheets

(51) Int. Cl.
*G06Q 10/00* (2012.01)
*A61M 5/44* (2006.01)

(58) Field of Classification Search
USPC .............. 219/394, 413, 491, 494, 385, 506;
604/111, 113; 705/2
See application file for complete search history.

(56) References Cited

U.S. PATENT DOCUMENTS

| | | |
|---|---|---|
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,659,719 A | 2/1928 | Blake |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,175,099 A | 10/1939 | Abbott |
| 2,204,764 A | 6/1940 | Mayo |
| 2,214,215 A | 9/1940 | Watermann et al. |
| 2,254,994 A | 9/1941 | Butland |
| 2,357,692 A | 9/1944 | Saffady |
| 2,470,481 A | 5/1949 | Freeman |
| 2,576,874 A | 11/1951 | Acton |
| 2,701,789 A | 2/1955 | White |
| 2,713,112 A | 7/1955 | Mills et al. |
| 2,741,099 A | 4/1956 | Beane |
| 2,766,907 A | 10/1956 | Wallace, Jr. |
| 2,841,132 A | 7/1958 | Philipp |
| 2,880,764 A | 4/1959 | Pelavin |
| 2,885,526 A | 5/1959 | Paulding |
| 2,910,981 A | 11/1959 | Wilson et al. |
| 2,990,875 A | 7/1961 | Samuels et al. |
| 2,994,760 A | 8/1961 | Pecoraro et al. |
| 3,051,582 A | 8/1962 | Muckier et al. |
| 3,140,716 A | 7/1964 | Harrison et al. |
| 3,157,727 A | 11/1964 | Hardy et al. |
| 3,193,339 A | 7/1965 | Cooper |
| 3,241,603 A | 3/1966 | Nagata |
| 3,247,851 A | 4/1966 | Seibert |
| 3,255,812 A | 6/1966 | Bayane et al. |
| 3,293,868 A | 12/1966 | Gonzalez |
| 3,329,202 A | 7/1967 | Birman |
| 3,353,589 A | 11/1967 | Tope et al. |
| 3,370,153 A | 2/1968 | Du Fresne et al. |
| 3,386,498 A | 6/1968 | Funfstuck |
| 3,475,590 A | 10/1969 | Pins |
| 3,485,245 A | 12/1969 | Lahr et al. |
| 3,500,366 A | 3/1970 | Chesney et al. |
| 3,536,132 A | 10/1970 | Pecoraro et al. |
| 3,551,641 A | 12/1970 | Truhan |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,059 A | 10/1971 | Ersek |
| 3,612,165 A | 10/1971 | Haynes |
| 3,614,385 A | 10/1971 | Horstmann |
| 3,629,552 A | 12/1971 | Edging |
| 3,640,277 A | 2/1972 | Adelberg |
| 3,651,695 A | 3/1972 | Brown |
| 3,704,625 A | 12/1972 | Seto et al. |
| 3,713,302 A | 1/1973 | Reviel |
| 3,777,187 A | 12/1973 | Kohn |
| 3,801,278 A | 4/1974 | Wagner et al. |
| 3,826,305 A | 7/1974 | Fishman |
| 3,858,106 A | 12/1974 | Launius |
| 3,861,213 A | 1/1975 | Parker |
| 3,864,976 A | 2/1975 | Parker |
| 3,879,171 A | 4/1975 | Tulis |
| 3,895,741 A | 7/1975 | Nugent |
| 3,908,652 A | 9/1975 | Weissinger |
| 3,940,742 A | 2/1976 | Hudspeth et al. |
| 4,024,377 A | 5/1977 | Henke |
| 4,038,519 A | 7/1977 | Foucras |
| 4,063,551 A | 12/1977 | Sweeney |
| 4,084,080 A | 4/1978 | McMahan |
| 4,090,514 A | 5/1978 | Hinck et al. |
| 4,098,123 A | 7/1978 | Granzow, Jr. |
| 4,167,663 A | 9/1979 | Granzow, Jr. et al. |
| 4,189,995 A | 2/1980 | Lohr et al. |
| 4,233,495 A | 11/1980 | Scoville et al. |
| 4,293,762 A | 10/1981 | Ogawa |
| 4,309,592 A | 1/1982 | Le Boeuf |
| 4,314,484 A | 2/1982 | Bowman |
| 4,318,276 A | 3/1982 | Sato et al. |
| 4,328,676 A | 5/1982 | Reed |
| 4,331,859 A | 5/1982 | Thomas et al. |
| 4,336,435 A | 6/1982 | Kashyap et al. |
| 4,356,383 A | 10/1982 | Dahlberg |
| 4,364,234 A | 12/1982 | Reed |
| 4,375,813 A | 3/1983 | Hessel |
| 4,384,578 A | 5/1983 | Winkler |
| 4,397,648 A | 8/1983 | Knute |
| 4,407,133 A | 10/1983 | Edmonson |
| 4,408,905 A | 10/1983 | Ehrenkranz |
| 4,419,568 A | 12/1983 | VanOverloop |
| 4,430,077 A | 2/1984 | Mittleman et al. |
| 4,430,078 A | 2/1984 | Sprague |
| 4,432,761 A | 2/1984 | Dawe |
| 4,448,204 A | 5/1984 | Lichtenstein |
| 4,455,478 A | 6/1984 | Guibert |
| 4,464,563 A | 8/1984 | Jewett |
| 4,468,137 A | 8/1984 | Hilsum et al. |
| 4,476,877 A | 10/1984 | Barker |
| 4,481,410 A | 11/1984 | Bortnik |
| 4,490,884 A | 1/1985 | Vickers |
| 4,495,402 A | 1/1985 | Burdick et al. |
| 4,498,901 A | 2/1985 | Finch |
| 4,509,532 A | 4/1985 | DeVries |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,531,941 A | 7/1985 | Zasuwa |
| 4,532,414 A | 7/1985 | Shah et al. |
| 4,533,350 A | 8/1985 | Danby et al. |
| 4,551,136 A | 11/1985 | Mandl |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,673,820 A | 6/1987 | Kamen |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,682,979 A | 7/1987 | Girouard |

(56) References Cited

U.S. PATENT DOCUMENTS

| | | |
|---|---|---|
| 4,684,367 A | 8/1987 | Schaffer et al. |
| 4,705,505 A | 11/1987 | Fried |
| 4,707,587 A | 11/1987 | Greenblatt |
| 4,709,135 A | 11/1987 | Dietrich et al. |
| 4,718,896 A | 1/1988 | Arndt et al. |
| 4,726,193 A | 2/1988 | Burke et al. |
| 4,735,609 A | 4/1988 | Comeau et al. |
| 4,745,248 A | 5/1988 | Hayes |
| 4,747,450 A | 5/1988 | Ikegame et al. |
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,554 A | 4/1989 | Trachtenberg et al. |
| 4,823,833 A | 4/1989 | Hogan et al. |
| 4,832,689 A | 5/1989 | Mauerer et al. |
| 4,844,074 A | 7/1989 | Kurucz |
| 4,844,397 A | 7/1989 | Skakoon et al. |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,878,588 A | 11/1989 | Ephraim |
| 4,883,117 A | 11/1989 | Dobbs et al. |
| 4,894,207 A | 1/1990 | Archer et al. |
| 4,900,308 A | 2/1990 | Verkaart |
| 4,904,848 A | 2/1990 | Colevas |
| 4,906,816 A | 3/1990 | Van Leerdam |
| 4,910,386 A | 3/1990 | Johnson |
| 4,916,386 A | 4/1990 | Schulz |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,000,581 A | 3/1991 | Yata et al. |
| 5,013,889 A | 5/1991 | Bakke |
| 5,019,047 A | 5/1991 | Kriesel |
| 5,040,380 A | 8/1991 | Gregory |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knopf et al. |
| 5,063,994 A | 11/1991 | Verkaart |
| 5,073,167 A | 12/1991 | Carr et al. |
| 5,074,658 A | 12/1991 | Tavlarides et al. |
| 5,075,167 A | 12/1991 | Yamauchi et al. |
| 5,081,697 A | 1/1992 | Manella |
| 5,096,078 A | 3/1992 | McQueeny |
| 5,096,822 A | 3/1992 | Rosenkrans, Jr. et al. |
| 5,097,898 A | 3/1992 | Verkaart |
| 5,103,817 A | 4/1992 | Reisdorf et al. |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,152,755 A | 10/1992 | Yoshinori |
| 5,153,827 A | 10/1992 | Coutre et al. |
| 5,169,389 A | 12/1992 | Kriesel |
| 5,180,896 A | 1/1993 | Gibby et al. |
| 5,183,994 A | 2/1993 | Bowles, Sr. et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,217,064 A | 6/1993 | Kellow et al. |
| 5,232,439 A | 8/1993 | Campbell et al. |
| 5,241,951 A | 9/1993 | Mason et al. |
| 5,243,172 A | 9/1993 | Hazan et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears et al. |
| 5,263,323 A | 11/1993 | Maus et al. |
| 5,263,929 A | 11/1993 | Falcone et al. |
| 5,269,749 A | 12/1993 | Koturov |
| 5,276,310 A | 1/1994 | Schmidt et al. |
| 5,279,558 A | 1/1994 | Kriesel |
| 5,279,598 A | 1/1994 | Sheaff |
| 5,282,264 A | 1/1994 | Reeves et al. |
| 5,282,683 A | 2/1994 | Brett |
| 5,290,222 A | 3/1994 | Feng et al. |
| 5,290,230 A | 3/1994 | Ainsworth et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,318,540 A | 6/1994 | Athayde et al. |
| 5,330,431 A | 7/1994 | Herskowitz |
| 5,333,326 A | 8/1994 | Faries, Jr. et al. |
| 5,338,157 A | 8/1994 | Blomquist |
| 5,342,313 A | 8/1994 | Campbell et al. |
| 5,345,923 A | 9/1994 | Luebke et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,415,282 A | 5/1995 | Kienholz |
| 5,417,274 A | 5/1995 | Verkaart |
| 5,420,962 A | 5/1995 | Bakke |
| 5,423,759 A | 6/1995 | Campbell |
| 5,424,512 A | 6/1995 | Turetta et al. |
| 5,433,704 A | 7/1995 | Ross et al. |
| 5,451,209 A | 9/1995 | Ainsworth et al. |
| 5,474,538 A | 12/1995 | Stihler et al. |
| 5,482,373 A | 1/1996 | Hutchinson |
| 5,483,799 A | 1/1996 | Dalto |
| 5,485,408 A | 1/1996 | Blomquist |
| 5,492,534 A | 2/1996 | Athayde et al. |
| 5,494,196 A | 2/1996 | Tyner |
| 5,512,043 A | 4/1996 | Verkaart |
| 5,514,095 A | 5/1996 | Brightbill et al. |
| 5,523,055 A | 6/1996 | Hansen et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,575,563 A | 11/1996 | Chiu et al. |
| 5,584,811 A | 12/1996 | Ross et al. |
| 5,590,648 A | 1/1997 | Mitchell et al. |
| 5,609,784 A | 3/1997 | Davenport |
| RE35,501 E | 5/1997 | Ross et al. |
| 5,634,426 A | 6/1997 | Tomlinson et al. |
| 5,647,854 A | 7/1997 | Olsen et al. |
| 5,649,910 A | 7/1997 | Kriesel et al. |
| 5,653,905 A | 8/1997 | McKinney |
| 5,658,250 A | 8/1997 | Blomquist et al. |

(56) References Cited

U.S. PATENT DOCUMENTS

| | | |
|---|---|---|
| 5,658,252 A | 8/1997 | Johnson |
| 5,658,478 A | 8/1997 | Roeschel et al. |
| 5,661,978 A | 9/1997 | Holmes et al. |
| 5,669,877 A | 9/1997 | Blomquist |
| 5,678,925 A | 10/1997 | Garmaise et al. |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |
| 5,707,151 A | 1/1998 | Parker et al. |
| 5,707,431 A | 1/1998 | Verkaart et al. |
| 5,713,864 A | 2/1998 | Verkart |
| 5,720,728 A | 2/1998 | Ford |
| 5,729,653 A | 3/1998 | Magliochetti et al. |
| 5,733,263 A | 3/1998 | Wheatman |
| 5,738,442 A | 4/1998 | Paron et al. |
| 5,743,878 A | 4/1998 | Ross et al. |
| 5,744,806 A | 4/1998 | Frojd |
| 5,755,275 A | 5/1998 | Rose et al. |
| 5,772,409 A | 6/1998 | Johnson |
| 5,779,364 A | 7/1998 | Cannelongo et al. |
| 5,786,568 A | 7/1998 | McKinney |
| 5,788,669 A | 8/1998 | Peterson |
| 5,788,671 A | 8/1998 | Johnson |
| 5,805,455 A | 9/1998 | Lipps |
| 5,806,528 A | 9/1998 | Magliochetti |
| 5,807,332 A | 9/1998 | Augustine et al. |
| 5,810,771 A | 9/1998 | Blomquist |
| 5,816,797 A | 10/1998 | Shoenfeld |
| 5,817,146 A | 10/1998 | Augustine |
| 5,823,746 A | 10/1998 | Johnson |
| 5,824,000 A | 10/1998 | Pavlo et al. |
| 5,840,068 A | 11/1998 | Cartledge |
| 5,858,303 A | 1/1999 | Schiffmann et al. |
| 5,862,672 A | 1/1999 | Faries, Jr. et al. |
| 5,875,282 A | 2/1999 | Jordan et al. |
| 5,876,370 A | 3/1999 | Blomquist |
| 5,879,143 A | 3/1999 | Cote et al. |
| 5,879,329 A | 3/1999 | Ginsburg |
| 5,891,096 A | 4/1999 | Hyun et al. |
| 5,893,843 A | 4/1999 | Rodrigues |
| 5,897,207 A | 4/1999 | Hartmann |
| 5,910,210 A | 6/1999 | Violi et al. |
| 5,919,218 A | 7/1999 | Carr |
| 5,924,289 A | 7/1999 | Bishop, II |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,700 A | 9/1999 | Kovelman |
| 5,961,492 A | 10/1999 | Kriesel et al. |
| 5,961,700 A | 10/1999 | Oliver |
| 5,961,866 A | 10/1999 | Hansen |
| 5,977,520 A | 11/1999 | Madson, Jr. et al. |
| 5,986,239 A | 11/1999 | Corrigan, III et al. |
| 5,989,238 A | 11/1999 | Ginsburg |
| 5,997,927 A | 12/1999 | Gics |
| 6,024,539 A | 2/2000 | Blomquist |
| 6,035,102 A | 3/2000 | Bakke |
| 6,039,926 A | 3/2000 | Goldman |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,123,827 A | 9/2000 | Wong et al. |
| 6,124,572 A | 9/2000 | Spilger et al. |
| 6,129,702 A | 10/2000 | Woias et al. |
| 6,139,528 A | 10/2000 | Kistner et al. |
| 6,142,974 A | 11/2000 | Kistner et al. |
| 6,146,359 A | 11/2000 | Carr et al. |
| 6,158,458 A | 12/2000 | Ryan |
| 6,164,469 A | 12/2000 | Sartore |
| 6,174,300 B1 | 1/2001 | Kriesel et al. |
| 6,175,099 B1 | 1/2001 | Shei et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,248,077 B1 | 6/2001 | Elson et al. |
| 6,254,572 B1 | 7/2001 | Knipfer et al. |
| 6,257,759 B1 | 7/2001 | Witonsky et al. |
| 6,259,067 B1 | 7/2001 | Faries, Jr. et al. |
| 6,261,261 B1 | 7/2001 | Gordon |
| 6,264,049 B1 | 7/2001 | Shteynberg |
| 6,294,762 B1 | 9/2001 | Faries, Jr. et al. |
| 6,315,767 B1 | 11/2001 | Dumont et al. |
| 6,316,750 B1 | 11/2001 | Levin |
| 6,334,707 B1 | 1/2002 | Ku |
| 6,371,121 B1 | 4/2002 | Faries, Jr. et al. |
| 6,376,805 B2 | 4/2002 | Faries, Jr. et al. |
| 6,384,380 B1 | 5/2002 | Faries, Jr. et al. |
| 6,464,666 B1 | 10/2002 | Augustine |
| 6,467,953 B1 | 10/2002 | Faries, Jr. et al. |
| 6,524,239 B1 | 2/2003 | Reed et al. |
| 6,553,336 B1 | 4/2003 | Johnson et al. |
| 6,566,631 B2 * | 5/2003 | Faries, Jr. ............ G01K 11/12 219/386 |
| 6,607,027 B2 | 8/2003 | Bosch et al. |
| 6,641,556 B1 | 11/2003 | Shigezawa |
| 6,641,602 B2 | 11/2003 | Balding |
| 6,649,040 B1 | 11/2003 | Mirchi et al. |
| 6,660,974 B2 | 12/2003 | Faries, Jr. et al. |
| 6,722,782 B2 | 4/2004 | Faries, Jr. et al. |
| 6,736,788 B1 | 5/2004 | Montgomery et al. |
| 6,740,059 B2 | 5/2004 | Flaherty |
| 6,748,164 B1 | 6/2004 | Kuzyk |
| 6,768,085 B2 | 7/2004 | Faries, Jr. et al. |
| 6,788,885 B2 | 9/2004 | Mitsunaga |
| 6,788,997 B1 | 9/2004 | Frederick |
| 6,824,528 B1 | 11/2004 | Faries, Jr. et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 6,967,575 B1 | 11/2005 | Dohrmann et al. |
| 6,987,452 B2 * | 1/2006 | Yang ............ A47G 29/141 232/36 |
| 7,031,602 B2 | 4/2006 | Faries, Jr. et al. |
| 7,031,778 B2 | 4/2006 | Hsiung et al. |
| 7,041,941 B2 * | 5/2006 | Faries, Jr. ............ A61M 5/445 128/898 |
| 7,090,658 B2 | 8/2006 | Faries, Jr. et al. |
| 7,176,030 B2 | 2/2007 | Faries, Jr. et al. |
| 7,238,171 B2 | 7/2007 | Faries, Jr. et al. |
| 7,262,698 B1 | 8/2007 | Frederick et al. |
| 7,276,675 B2 * | 10/2007 | Faries, Jr. ............ A61M 5/445 219/385 |
| 7,307,245 B2 | 12/2007 | Faries, Jr. et al. |
| 7,326,882 B2 | 2/2008 | Faries, Jr. et al. |
| 7,328,654 B2 * | 2/2008 | Shei ............ A47J 39/006 219/385 |
| 7,417,205 B2 | 8/2008 | Faries, Jr. et al. |
| 7,540,864 B2 | 6/2009 | Faries, Jr. et al. |
| 7,608,460 B2 | 10/2009 | Reed et al. |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries et al. |
| 8,444,599 B2 | 5/2013 | Faries, Jr. et al. |
| 8,487,738 B2 | 7/2013 | Faries, Jr. et al. |
| 8,636,691 B2 | 1/2014 | Faries, Jr. |
| 8,734,404 B2 | 5/2014 | Faries, Jr. |
| 8,734,405 B2 | 5/2014 | Faries, Jr. |
| 8,821,011 B2 | 9/2014 | Faries, Jr. et al. |
| 8,845,586 B2 | 9/2014 | Faries, Jr. et al. |
| 8,920,372 B2 | 12/2014 | Faries, Jr. et al. |
| 8,920,387 B2 | 12/2014 | Faries, Jr. et al. |
| 2001/0009610 A1 | 7/2001 | Augustine |
| 2002/0081109 A1 | 6/2002 | Mitsunaga et al. |
| 2002/0147426 A1 | 10/2002 | Faries, Jr. et al. |
| 2002/0151854 A1 | 10/2002 | Duchon et al. |
| 2002/0156451 A1 | 10/2002 | Lenker |

(56) References Cited

U.S. PATENT DOCUMENTS

| | | |
|---|---|---|
| 2002/0158058 A1* | 10/2002 | Faries, Jr. ............. A61F 7/0241 219/400 |
| 2002/0184906 A1 | 12/2002 | Faries, Jr. et al. |
| 2003/0000939 A1 | 1/2003 | Faries et al. |
| 2003/0004470 A1 | 1/2003 | Hickerson et al. |
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0218003 A1 | 11/2003 | Ellis et al. |
| 2003/0222933 A1 | 12/2003 | Choi |
| 2004/0170409 A1 | 9/2004 | Faries, Jr. et al. |
| 2004/0189258 A1 | 9/2004 | Lehmann et al. |
| 2004/0247016 A1 | 12/2004 | Faries, Jr. et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0241026 A1* | 10/2005 | Esler ............. G06Q 50/22 705/2 |
| 2005/0242930 A1 | 11/2005 | Nicolson et al. |
| 2006/0020255 A1 | 1/2006 | Cassidy et al. |
| 2006/0100578 A1 | 5/2006 | Lieberman |
| 2006/0253075 A1 | 11/2006 | Faries, Jr. et al. |
| 2006/0291533 A1 | 12/2006 | Faries, Jr. et al. |
| 2007/0000910 A1 | 1/2007 | Faries, Jr. et al. |
| 2007/0015975 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0197878 A1* | 8/2007 | Shklarski ........... A61B 5/02055 600/300 |
| 2007/0215018 A1 | 9/2007 | Faries, Jr. et al. |
| 2008/0021392 A1 | 1/2008 | Lurvey et al. |
| 2008/0058697 A1 | 3/2008 | Kamen et al. |
| 2008/0147016 A1 | 6/2008 | Faries et al. |
| 2008/0205481 A1 | 8/2008 | Faries et al. |
| 2009/0082726 A1* | 3/2009 | Ogawa .................... A61M 5/44 604/114 |
| 2010/0059498 A1 | 3/2010 | Hansen et al. |
| 2010/0082459 A1 | 4/2010 | Tusa et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2011/0030565 A1* | 2/2011 | Shei ..................... A47J 39/006 99/329 P |
| 2011/0297831 A1 | 12/2011 | Yao et al. |
| 2011/0307274 A1 | 12/2011 | Thompson et al. |
| 2012/0053518 A1 | 3/2012 | Faries, Jr. et al. |
| 2012/0191050 A1 | 7/2012 | Faries, Jr. et al. |
| 2012/0265336 A1 | 10/2012 | Mallett et al. |
| 2012/0285236 A1 | 11/2012 | Haartsen et al. |
| 2013/0197437 A1 | 8/2013 | Faries et al. |
| 2013/0253952 A1 | 9/2013 | Burke et al. |
| 2014/0236615 A1 | 8/2014 | Ragusky et al. |

FOREIGN PATENT DOCUMENTS

| | | |
|---|---|---|
| EP | 0927552 A1 | 7/1999 |
| GB | 2029677 A | 3/1980 |
| GB | 2274514 | 7/1994 |
| JP | 58-030666 | 2/1983 |
| JP | 2000-300666 | 10/2000 |
| NZ | 331678 A | 3/2000 |
| WO | 9221272 | 12/1992 |
| WO | 98/38953 A1 | 9/1998 |
| WO | 98/45658 A1 | 10/1998 |
| WO | 9845658 | 10/1998 |
| WO | 99/22786 A1 | 5/1999 |
| WO | 99/58177 A1 | 11/1999 |

OTHER PUBLICATIONS

Minco Products, Inc., Bulletin CT198, 1996.
Eurotherm Controls, Inc., Model 2116 Temperature Controller, 1997.
Ellenwood, Drop Detector, IBM Technical Bulletin, vol. 12, No. 5, Oct. 1969.
Cbi Medical, Inc., IV Fluid Warmer Model 8362, 1992.
Cahill, New Name, New Helmsman, JEMS, Aug. 1996.
Cbi Healthcare Systems, Inc. Controlled Temperature Cabinet Syste, JEMS, Mar. 17, 1997.
Koolatron, P-34 PC-3 Precision Control Thermolectric Cooler/Warmer, Jan. 1998.
Koolatron, Canadian Company announces the release of a precision control unit, Aug. 1997.
Anton, 500 miles from nowhere, it'll give you a cold drink or a warm burger . . . , Technology Update, 1993.
Koolatron, 1997 U.S. $Price List, 1997.
Kellow et al, Drug Adulteration in Prehospital Emergency Medical Services, Oct. 1994.
PCT International Search Report and Written Opinion, PCT/US2014/015944, Jun. 2, 2014, 11 pages.
PCT International Search Report and Written Opinion, PCT/US2014/016869, Jun. 27, 2014, 10 pages.

* cited by examiner

TEMPERATURE REPORT

COMPANY              NAME
WARMER MODEL         MODEL
WARMER SERIAL NUMBER 1234
UNITS                °F
REPORT DATE          MM/DD/YYYY 12:00:00 TO MM/DD/YYYY 19:00:00

SUMMARY
NUMBER OF WARNING MESSAGES*       0
MAX BAG TEMPERATURE               104 °F
MIN BAG TEMPERATURE               74 °F
NUMBER OF BAGS EXCEEDING 107°F    0 BAG(S)
MAX NUMBER OF DAYS OF WARMING     12 DAY(S)
NUMBER OF BAGS WARMED             100 BAG(S)

*SEE COLUMN H FOR WARNING MESSAGES

| READING NO | DATE & TIME | SET POINT | TRAY 1 | TRAY 2 | • • • | TRAY 16 | WARNINGS |
|---|---|---|---|---|---|---|---|
| 1 | MM/DD/YYYY 12:00:00 | 104 | 79 | 79 | | 79 | |
| 2 | MM/DD/YYYY 13:00:00 | 104 | 104 | 104 | | 104 | |
| 3 | MM/DD/YYYY 14:00:00 | 104 | RELOAD | 104 | | 104 | |
| 4 | MM/DD/YYYY 15:00:00 | 104 | RELOAD | 104 | | 104 | |
| 5 | MM/DD/YYYY 16:00:00 | 104 | 74 | 104 | | 104 | |
| 6 | MM/DD/YYYY 17:00:00 | 104 | RELOAD | 104 | | RELOAD | |
| 7 | MM/DD/YYYY 18:00:00 | 104 | RELOAD | 104 | | RELOAD | |
| 8 | MM/DD/YYYY 19:00:00 | 104 | RELOAD | 104 | | RELOAD | |

PLURAL MEDICAL ITEM WARMING SYSTEM AND METHOD FOR WARMING A PLURALITY OF MEDICAL ITEMS TO DESIRED TEMPERATURES

CROSS-REFERENCE TO RELATED APPLICATIONS

This application claims priority to U.S. Provisional Patent Application Ser. No. 61/765,313, entitled "Plural Medical Item Warming System and Method For Warming a Plurality of Medical. Items to Desired Temperatures", and filed Feb. 15, 2013, the disclosure of which is incorporated herein by reference in its entirety.

BACKGROUND

1. Technical Field

Present invention embodiments pertain to thermally treating medical or other items and, more specifically, to a thermal treatment system including a modular configuration with a control unit and one or more modular units coupled to the control unit to thermally treat a plurality of medical items.

2. Discussion of Related Art

Various types of medical items require heating to a selected temperature prior to utilization in a medical procedure. In particular, medical items, such as intravenous (IV) fluid bags, are typically heated to precise temperatures to prevent thermal shock and injury from occurring during infusion of such IV fluid into a patient. In order to provide the necessary heated items for use in certain medical procedures, medical personnel typically utilize a warming system to heat items toward their operational temperatures. However, conventional warming systems may enable use of items having temperatures incompatible with a medical procedure, may require a substantial time interval to heat items to desired temperatures, may heat articles in an uneven manner enabling formation of hot spots, and may even operate absent items placed therein. In addition, the warming systems typically employ a non-expandable structure with a limited capacity for medical items.

SUMMARY

Present invention embodiments include a thermal treatment system for thermally treating and individually monitoring a plurality of medical or other items. The thermal treatment system includes a modular configuration with a control unit and one or more modular units coupled to the control unit, where each of the control and modular units thermally treat a plurality of corresponding medical items. The control unit includes a display to interact with a user for setting a desired temperature, and controls the modular units to thermally treat corresponding medical items to the desired temperature.

The above and still further features and advantages of the present invention will become apparent upon consideration of the following detailed description of example embodiments thereof, particularly when taken in conjunction with the accompanying drawings, wherein like reference numerals in the various figures are utilized to designate like components.

BRIEF DESCRIPTION OF THE DRAWINGS

FIG. 11 is an example report produced by the control unit according to an embodiment of the present invention.

DETAILED DESCRIPTION OF EXAMPLE EMBODIMENTS

Figure 1:
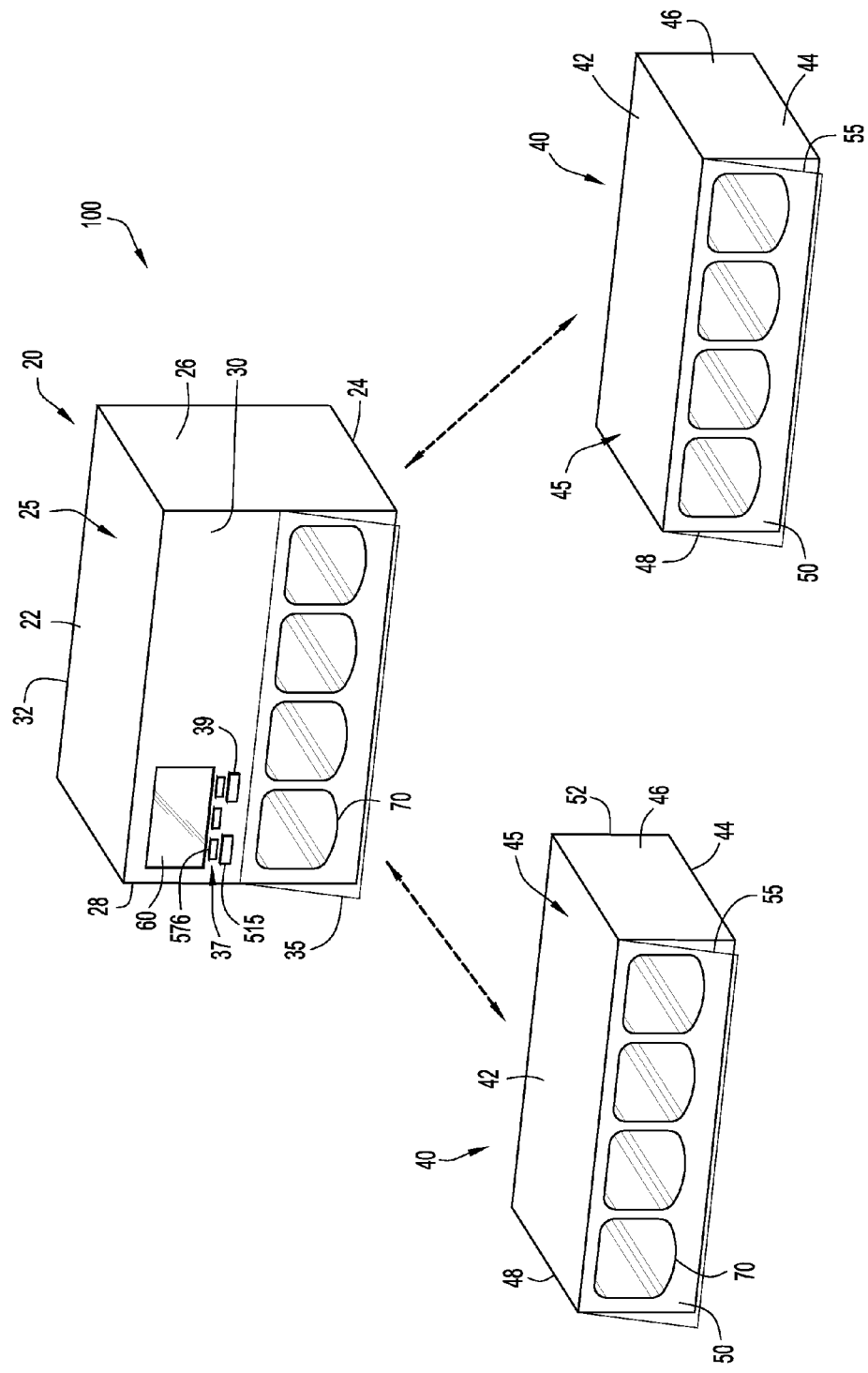
FIG. 1 is a diagrammatic illustration of an example thermal treatment system including a control unit and one or more modular units according to an embodiment of the present invention.

Present invention embodiments pertain to thermally treating medical or other items. A modular thermal treatment system for thermally treating and/or monitoring medical solution containers (e.g., bags or bottles containing saline or intravenous (IV) solutions, antibiotics or other drugs, blood, etc.) or other medical items (e.g., instruments, blankets, etc.) is illustrated in FIG. 1. Specifically, a thermal treatment system 100 includes a control unit 20, and one or more modular units 40. The control unit includes a unit housing 25 with a series of heating assemblies 70 each to thermally treat a corresponding medical or other item as described below. Housing 25 is generally in the form of a rectangular box, and includes top and bottom walls 22, 24, side walls 26, 28, front and rear walls 30, 32, and a door 35. The door and the front, rear, top, bottom and side walls are each substantially rectangular, where the walls and door collectively define a housing interior. Further, front wall 30 includes a control panel 37 disposed above the door. The control panel includes a display 60, input devices 576 (e.g., keys, buttons, switches, etc.) to facilitate entry of information (e.g., enter or adjust set point temperature, switch between Fahrenheit and Celsius, etc.), power switch 515 to enable power to the system, and a port 39 to receive a removable storage device for transferring information.

Heating assemblies 70 are preferably disposed within a lower portion of the housing interior, and may be mounted therein via any conventional or other mounting devices (e.g., rails, ledges, brackets, etc.). Door 35 includes a handle (not shown) or other gripping mechanism to enable pivoting of the door relative to the front wall for providing access to heating assemblies 70. The handle or gripping mechanism may be implemented by any conventional or other type of handle or gripping mechanism, and may be disposed on the door at any suitable location. Door 35 generally pivots toward and away from the housing front wall, and is preferably constructed of a substantially transparent material, such as glass or plexiglass, to further serve as a window to enable viewing of the medical items and maintain heat within the housing. The door may be of any size or shape. Further, control unit 20 includes a door lock 660 (FIG. 6) to secure door 35 in a closed state and control access to the medical items placed on the heating assemblies. The door lock is preferably actuated by entry of a code via display 60 and/or input devices 576, and may be implemented by any conventional or other door lock engaging the door and housing and/or heating assembly.

Each modular unit 40 includes a unit housing 45 with a series of heating assemblies 70 each to thermally treat a corresponding medical or other item as described below. Housing 45 is generally in the form of a rectangular box, and includes top and bottom walls 42, 44, side walls 46, 48, front and rear walls 50, 52, and a door 55. The door and the front, rear, top, bottom and side walls are each substantially rectangular, where the walls and door collectively define a housing interior.

Heating assemblies 70 of modular unit 40 are preferably disposed within a lower portion the housing interior, and may be mounted therein via any conventional or other mounting devices (e.g., rails, ledges, brackets, etc.). Door 55 includes a handle (not shown) or other gripping mechanism to enable pivoting of the door relative to the front wall for providing access to heating assemblies 70. The handle or gripping mechanism may be implemented by any conventional or other type of handle or gripping mechanism, and may be disposed on the door at any suitable location. Door 55 generally pivots toward and away from the housing front wall, and is preferably constructed of a substantially transparent material, such as glass or plexiglass, to further serve as a window to enable viewing of the medical items and maintain heat within the housing. The door may be of any size or shape. Further, modular unit 40 includes a door lock 660 (FIG. 8) to secure door 55 in a closed state and control access to the medical items. The door lock is preferably actuated by entry of a code via display 60 and/or input devices 576 of the control unit, and may be implemented by any conventional or other door lock engaging the door and housing and/or heating assembly.

Control unit 20 is coupled to each modular unit 40, and controls the modular units to thermally treat corresponding medical items to desired temperatures. By way of example only, the control and modular units each include four heating assemblies 70, where control unit 20 may be coupled to a maximum of three modular units 40. Thus, system configurations may be provided for accommodating a maximum of sixteen medical items (e.g., accommodating a maximum of four, eight, twelve or sixteen medical items). However, the control unit may be coupled to any quantity of modular units, where each of the control and modular units may include any quantity of heating assemblies. Further, the heating assemblies may include any sized heating plates to accommodate various sized medical solution containers (e.g., one liter, three liter, etc.) or other medical items. In the event of a power outage (or momentary interruption of power), control unit 20 is enabled automatically when power is restored. This minimizes cooling of the medical items due to a power outage.

Figure 10:
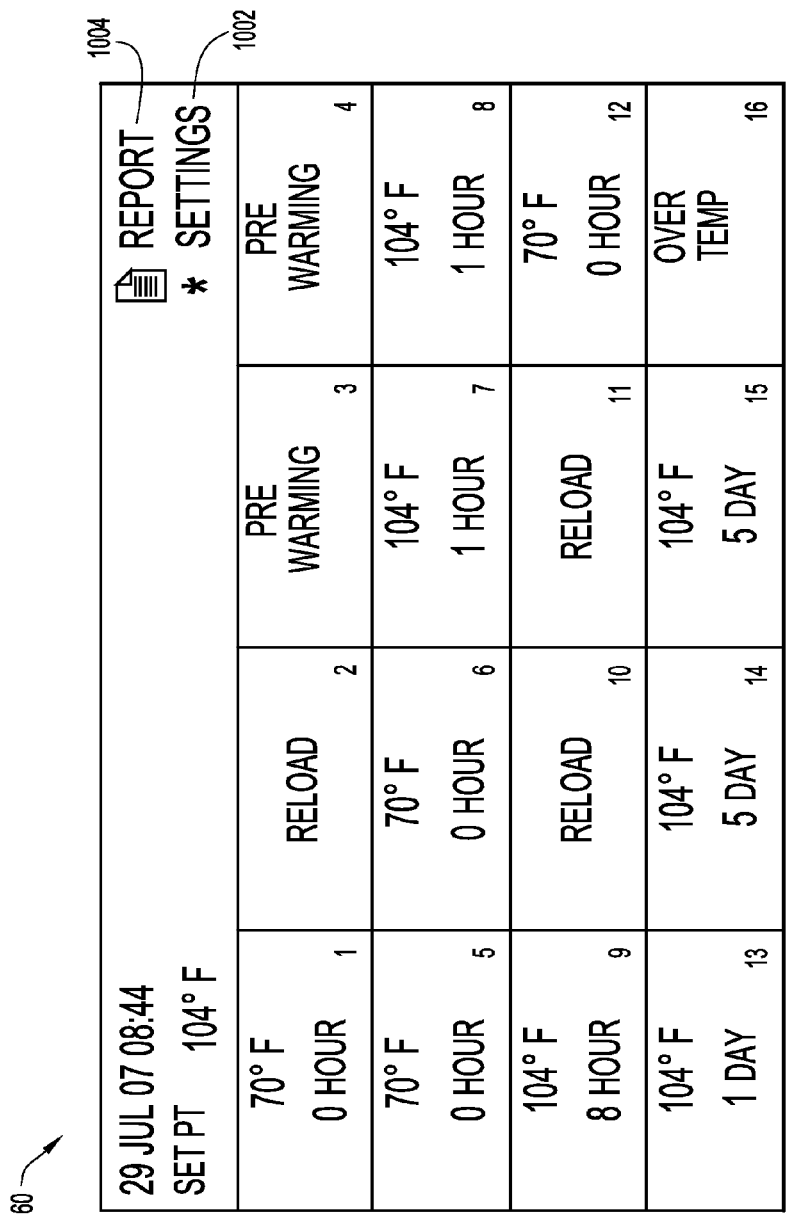
FIG. 10 is a diagrammatic illustration of an example display screen produced by the control unit according to an embodiment of the present invention.

Display 60 of control unit 20 is preferably implemented by a conventional touch-screen type of display (e.g., resistive, capacitive, etc.) to interact with, and provide and retrieve information from, a user. Display 60 is preferably disposed toward a side edge of front wall 30 of control unit 20. The user enters a desired temperature via display 60 and/or input devices 576, and the control unit controls heating assemblies 70 of the control and modular units to thermally treat the corresponding medical or other items to the desired temperature as described below. Display 60 further provides temperature and other information (FIG. 10). By way of example only, the desired or set point temperature may be in the range of 32°-104° F. The desired temperature is typically applicable to each heating assembly within the system. However, the system may alternatively receive two or more different desired temperatures for the heating assemblies to heat medical items to different temperatures.

In addition, the control unit may generate reports (FIG. 11) (e.g., set point and medical item temperature history and other information, etc.) that may be downloaded to a memory device (e.g., Universal Serial Bus (USB) or other drive, etc.) via port 39. The information may be removed from the system once the report is downloaded in order to conserve memory.

Figure 2:
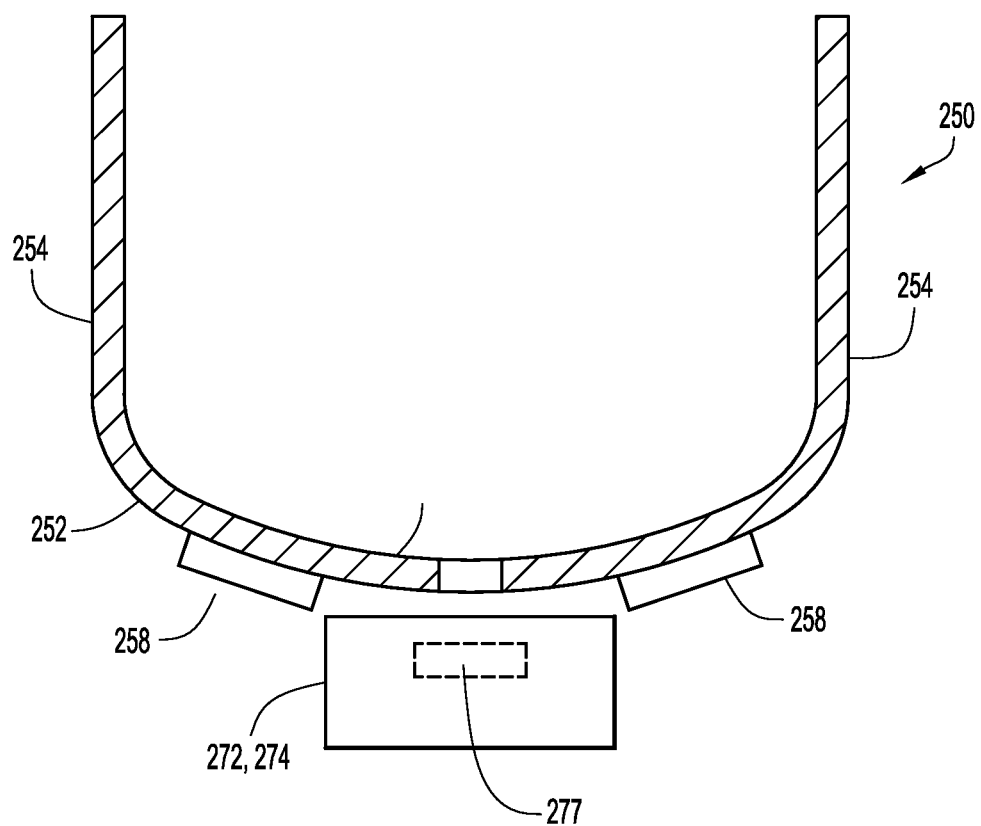
FIG. 2 is a side view in partial section of a heating assembly according to an embodiment of the present invention.

Referring to FIG. 2, each heating assembly 70 (e.g., of control unit 20 and modular units 40) includes a heating plate 250, a heater 258, temperature sensors 272, 274 and a presence sensor 277. The heating plate includes bottom wall 252 and side walls 254 extending from the bottom wall longer dimensioned side edges. The side walls extend in a substantially perpendicular manner from the bottom wall to form a generally 'U'-shaped heating plate configuration with rounded edges. Heater 258 is disposed on the bottom surface of the heating plate bottom wall. This arrangement facilitates rapid heating of a medical item which is especially advantageous during employment of the system in time critical situations, such as in an operating room. For example, the system may heat items to a desired temperature in the approximate range of 70° F. to 104° F. within +/−1° F.) within a short time interval, generally within one hour (e.g., less than 35 minutes in an ambient temperature of 70° F.; however, the particular time interval depends on various factors, such as initial item temperature, room temperature, selected desired temperature, etc.).

Figure 9:
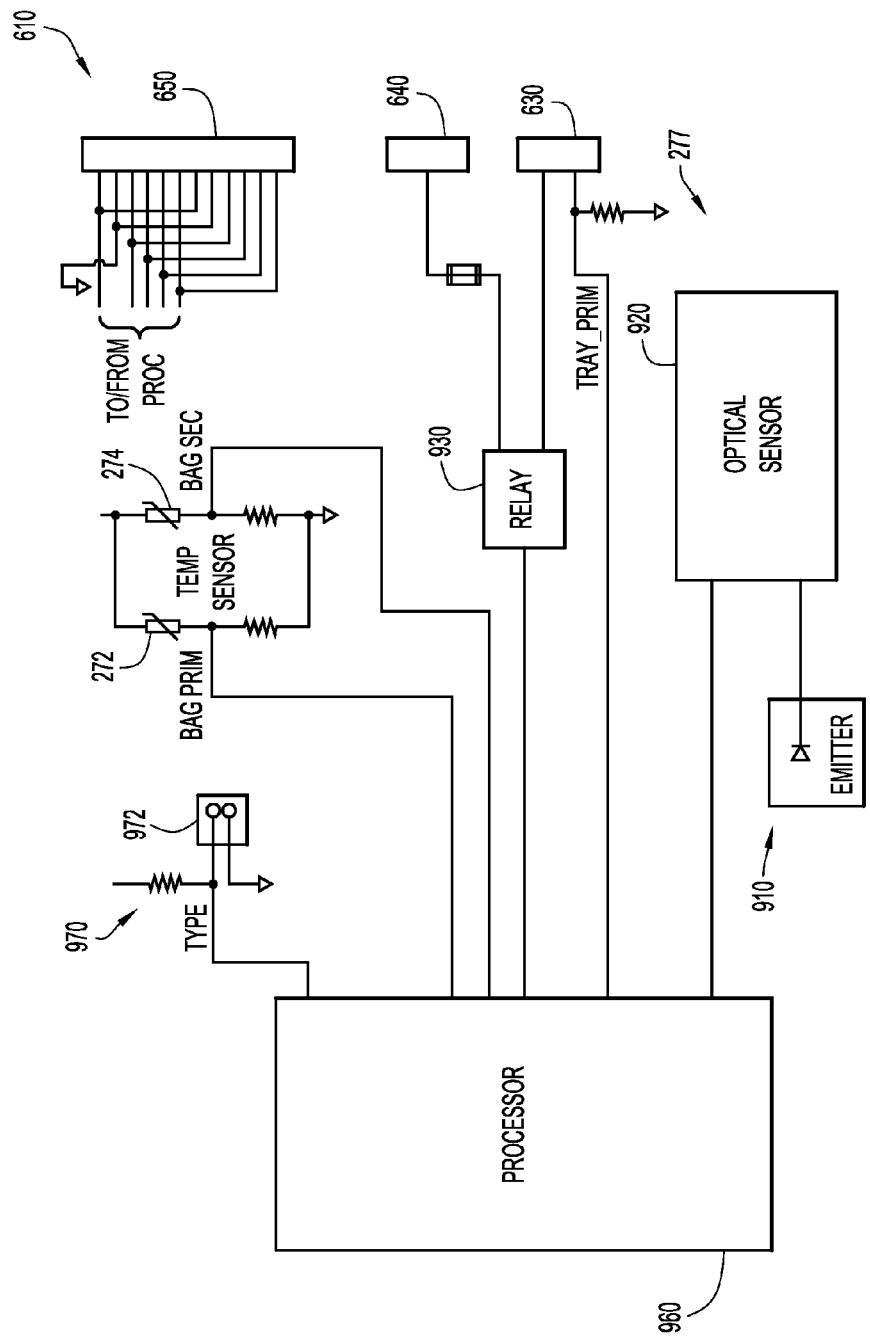
FIG. 9 is a schematic diagram of a heat assembly control circuit of the heat control circuits for the control and modular units according to an embodiment of the present invention.

Presence sensor 277 controls heater 258 in response to placement and removal of medical items (e.g., medical solution containers, etc.) on the heating plate. Specifically, the presence sensor is typically implemented in the form of an infrared or other optical sensor that enables or disables the heater in response to detection of the presence or absence of the medical item. Presence sensor 277 is disposed beneath the heating plate and includes an infrared transmitter 910 and receiver 920 that respectively emit and receive infrared signals (FIG. 9). Heating plate bottom wall 252 and heater 258 each include an opening defined therein to enable transmission and reception of the infrared signals and access to the medical item by temperature sensors 272, 2.74. When a medical item is present on the heating plate, infrared signals from the transmitter are emitted through the openings in the heating plate bottom wall and heater, and reflected back toward the receiver from the medical item. Thus, the presence of the medical item enables the receiver to detect a relatively strong infrared signal.

If a medical item is absent from the heating plate, infrared signals from the transmitter are emitted through the openings in the heating plate and heater and into the empty space about the plate. Thus, the receiver detects low or weak infrared signals (e.g., scattered by the surrounding area), thereby indicating the absence of a medical item on the heating plate.

Temperature sensors 272, 274 are mounted proximate heating plate 250, and preferably in contact with the medical item (e.g., through the openings of the heating plate and heater) to measure the temperature of the medical item (e.g., medical solution container and/or the medical solution therein). The openings of the heating plate bottom wall and heater provide temperature sensors 272, 274 with access to the medical item placed on the heating plate. In addition, a temperature sensor 286 (FIG. 7) is mounted on heater 258 to basically measure excessive temperatures of the heating plate, and serves as a cut-off switch as described below.

Figure 3:
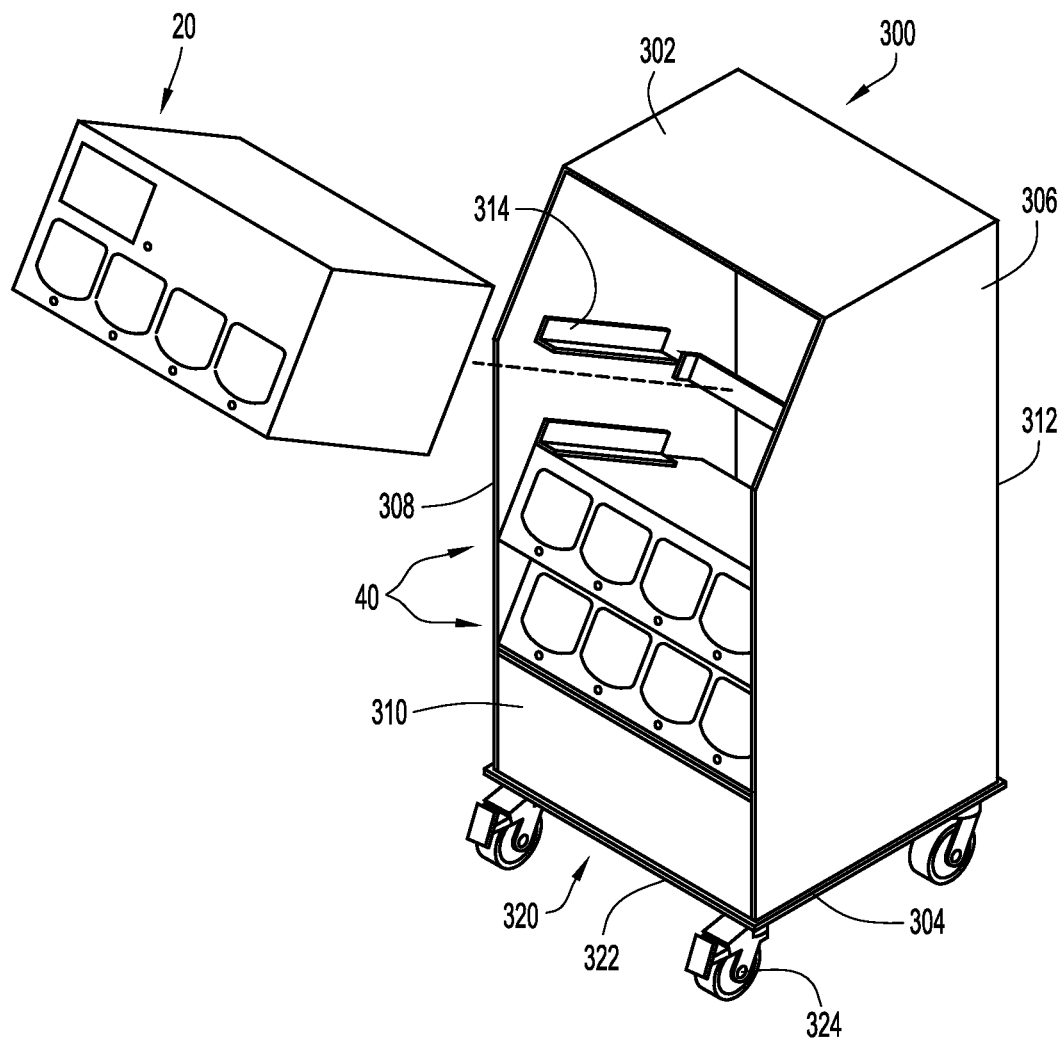
FIG. 3 is an exploded view in perspective of a cabinet structure housing a control unit and one or more modular units according to an embodiment of the present invention.

The control and modular units may be arranged in various fashions to thermally treat medical or other items. By way of example, the control and corresponding modular units may be placed within a cabinet structure as illustrated in FIG. 3. Specifically, a cabinet structure 300 is generally in the form of a rectangular box and includes top and bottom walls 302, 304, side walls 306, 308, a front wall 310 and a rear wall 312. The top, bottom, front and rear walls are each substantially rectangular, while the side walls are generally rectangular with a truncated upper front corner portion. Top wall 302 extends from rear wall 312 for a distance less than that between the rear wall and front wall. Front wall 310 is disposed at a lower portion of the cabinet structure between side walls 306, 308 and is attached to bottom wall 304. The walls collectively define a cabinet interior. The cabinet may be constructed of electro-galvanized steel or other suitably sturdy material, and may be of any size or shape.

Control unit 20 and modular units 40 are disposed within the cabinet interior, and are preferably mounted therein via rails or brackets 314 attached to the interior surfaces of side walls 306, 308. However, any conventional or other mounting devices (e.g., rails, ledges, brackets, etc.) may be employed within the cabinet interior. Rails 314 are generally 'L'-shaped and substantially aligned along the opposing side walls to provide a ledge for supporting the bottom walls of the control and modular units. Each pair of corresponding rails mounted on opposing sidewalls preferably supports a corresponding unit within the cabinet interior, where the rails are spaced vertically along each sidewall to arrange the control and modular units in a stacked relation. The control and modular units may be arranged or stacked in any desired order within the cabinet interior, where the modular units are coupled to the control unit. The rails are further oriented at a downward angle toward rear wall 312 in order to support the control and modular units in a similar (downward) orientation to maintain medical solution containers on the heating assemblies.

Cabinet structure 300 may include or reside on a support platform 320. The platform includes a substantially rectangular base to support cabinet 300 thereon. Rollers or casters 324 are attached to the underside of the base with each caster disposed toward a corresponding base corner to enable the support platform (and hence the cabinet containing the thermal treatments system) to be transportable. The casters or rollers may be of any quantity, may be implemented by any conventional or other types of rollers or wheel-type structures, and may be disposed at any locations on the base.

Figure 4:
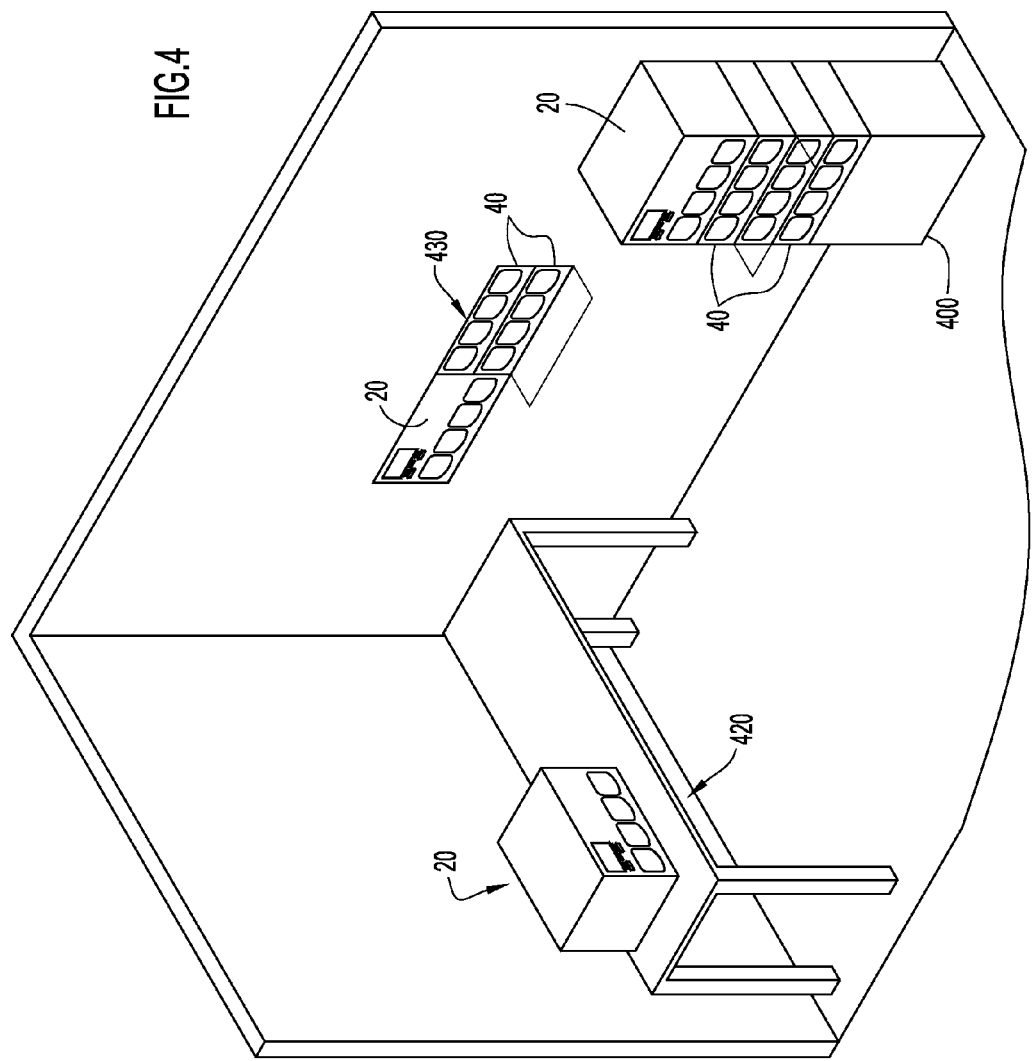
FIG. 4 is a view in perspective of various manners of deploying the thermal treatment system of FIG. 1 according to embodiments of the present invention.

Further examples of arrangements of the control and modular units are illustrated in FIG. 4. Specifically, the control and modular units may be arranged in a stacked relation with one unit supported by or resting on top of another. The control unit may be placed at any desired location within the stacked arrangement, and is coupled to the modular units. The stacked units are placed on the top surface of a pedestal 400 in the form of a substantially rectangular block to produce an operational arrangement.

Moreover, the control and/or modular units may be placed on a supporting surface. For example, control unit 20 may be placed on a table 420 or counter (as illustrated in FIG. 4) to enable operation. In addition, the control and modular units may be placed within an opening 430 in a wall of a room or other area to provide a recessed configuration for operation and to conserve space or area for the thermal treatment system.

In addition, the control and modular units may be local to each other and coupled via a type of wired medium (e.g., quick detach or other cabling and/or connectors, etc.). Alternatively, the control and modular units may be located remotely or separated and be coupled via a wireless medium. Further, the control unit may be accessible over a network (e.g., Wide Area Network (WAN), Local Area Network (LAN), Internet, Intranet, etc.) to receive settings and/or transmit generated reports.

Figure 5:
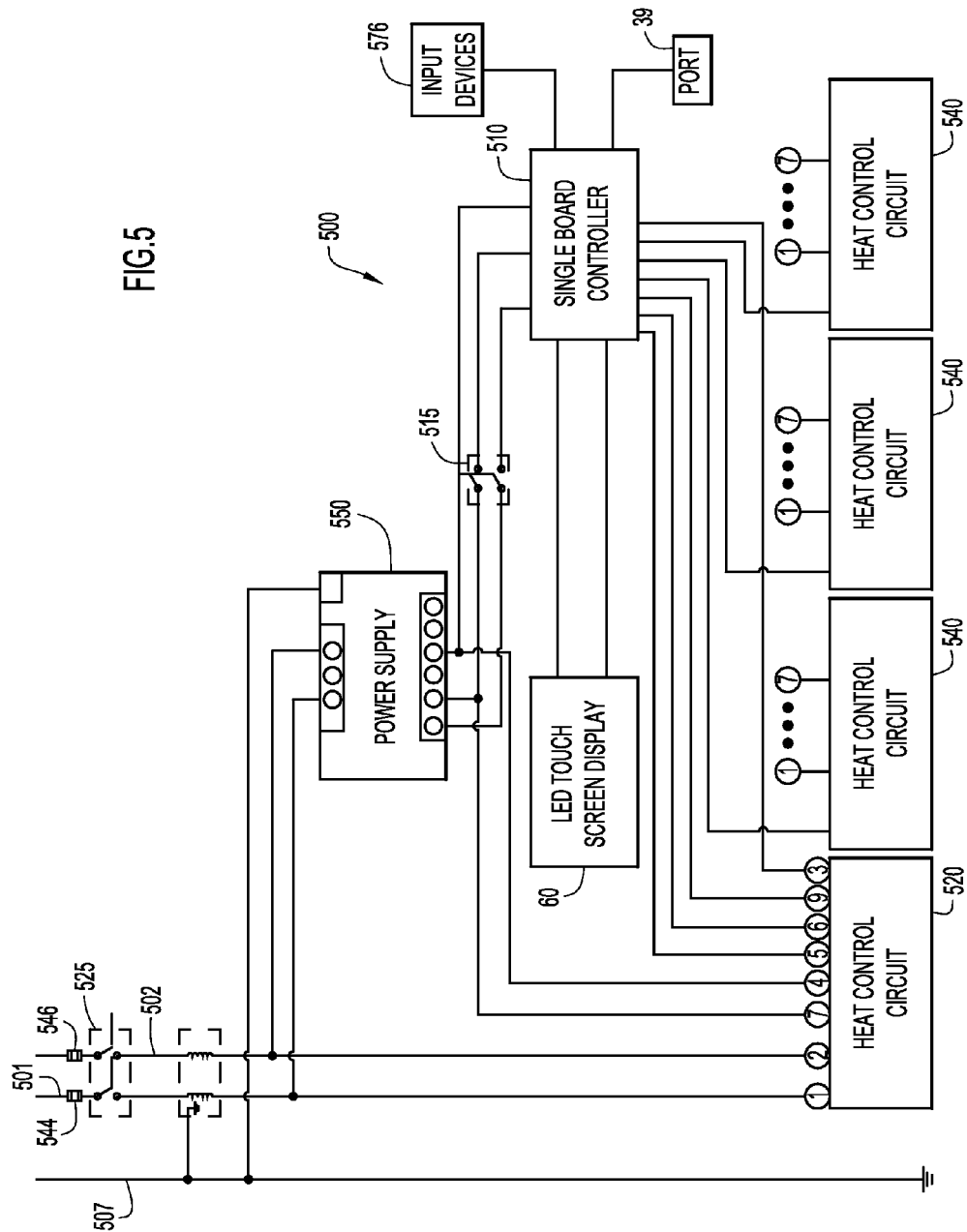
FIG. 5 is a schematic diagram of a control circuit for the thermal treatment system according to an embodiment of the present invention.

An example control circuit for the thermal treatment system according to an embodiment of the present invention is illustrated in FIG. 5. Specifically, a control circuit 500 is disposed within control unit 20 and includes power conductors 501, 502, a ground 507, front and rear power switches 515, 525, a system controller 510, display 60, a heat control circuit 520 for the control unit, and a power supply 550. The control circuit is further coupled to heat control circuits 540 each associated with a corresponding modular unit 40. The heat control circuits of the control and modular units individually control the heating assemblies of those units as described below.

Controller 510 typically includes a processor and accompanying circuitry. However, the system controller may be implemented by any conventional or other controller, processor and/or circuitry. Power conductors 501, 502 each include a respective fuse 544, 546 that is arranged in series with rear power switch 525 (preferably disposed on rear wall 22 of the control unit) to prevent power surges from damaging the switch and circuitry. Power switch 525 controls power to circuitry of the control circuit from power supply 550.

Controller 510 is connected to power supply 550, display 60, and input devices 576. Further, the system controller is connected to or in communication with heat control circuits 520, 540, where the communication or connection may be implemented in any desired fashion (e.g., wires, busses, etc.). The power supply provides appropriate power signals (e.g., 12V DC) to the system controller, while the system controller receives user information from input devices 576 and controls system operation based on the user information and system conditions (e.g., power enabled, etc.). Set point temperature and other information and power signals received by the system controller are distributed to heat control circuits 520, 540 to facilitate heating of medical items as described below.

The system controller receives residence time, medical item temperature and other information (e.g., excessive temperature detection, presence of a medical item, etc.) from the heat control circuits and controls display 60 to display information (e.g., residence time, medical item temperature, excessive temperature detections, reload or empty indications, etc.) for the heating assemblies. The display is generally partitioned into sections with each section associated with a corresponding heating assembly (e.g., the location of a section on the display preferably corresponds to the position of the associated heating assembly within the cabinet) to provide information pertaining to that assembly (FIG. 10). The heating assemblies may each be associated with an identifier (e.g., a reference number, 1-16, as viewed in FIG. 10) that appears on the display to associate displayed information with a corresponding heating assembly. However, the display may be arranged in any fashion to provide information to an operator.

Further, display 60 indicates when a medical item on a heating assembly has attained or is near (e.g., within a predetermined or user-specified range from) the desired or set point temperature. The indicator is preferably in the form of a colored bar or other object to indicate when the medical item temperature is below (e.g., the medical item is being warmed), at (or within a desired range from), or exceeds (e.g., beyond a desired range indicating an over temperature condition) the desired temperature. By way of example, the display provides a generally blue bar or object to indicate that a medical item is being warmed (e.g., medical item temperature is less than the set point temperature by more than 2° F.), a generally green bar or object to indicate that the medical item is within an acceptable range of the set point temperature (e.g., within +/−2° F. of the set point temperature) and ready for use, and a generally red bar or object when the medical item temperature is considered excessive (e.g., greater than the set point temperature by more than 2° F. (or greater than 106.5° F.). In the latter case of excessive temperature, display 60 further indicates an over temperature ("OVER TEMP") condition, and heater 258 of the heating assembly is disabled.

Figure 6:
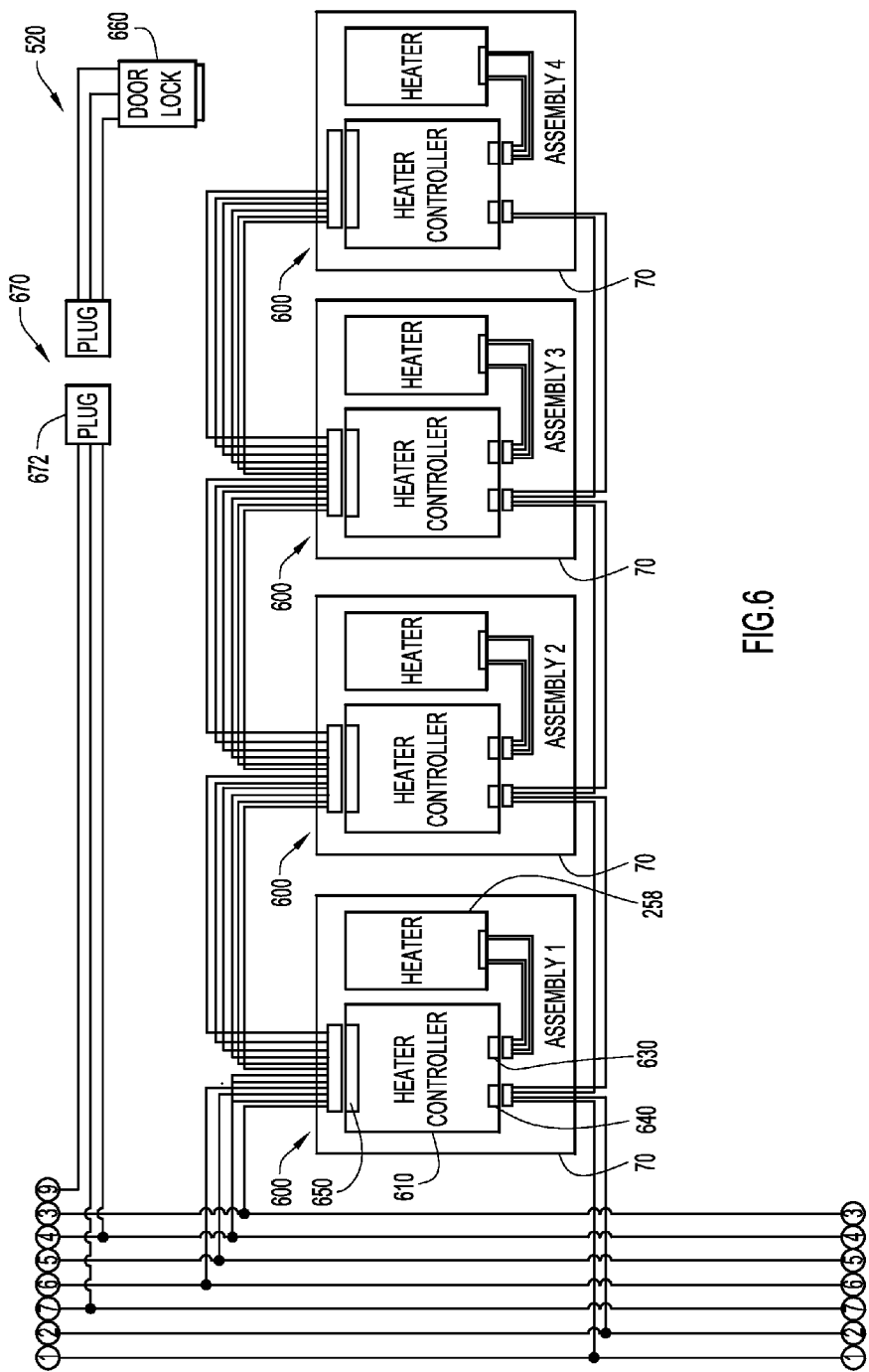
FIG. 6 is a schematic diagram of a heat control circuit of FIG. 5 for a control unit according to an embodiment of the present invention.

An example heat control circuit 520 of control unit 20 is illustrated in FIG. 6. Specifically, heat control circuit 520 receives information from system controller 510 to control corresponding heating assemblies 70 of control unit 20 (FIG. 1). In addition, control unit 20 includes door lock 660 controlling actuation of door 35 and access to the heating assemblies as described above. The door lock is controlled by signals received from system controller 510 via plugs or connectors 670, 672. The signals are based on entry of a proper code to transition door 35 between open and closed states and control access to the medical items. One or more codes may be utilized to control the door lock (e.g., a code may be utilized to place the door in an open state for a predetermined time interval, a code may be utilized to lock the door while another code may be used to open the door, etc.).

Figure 7:
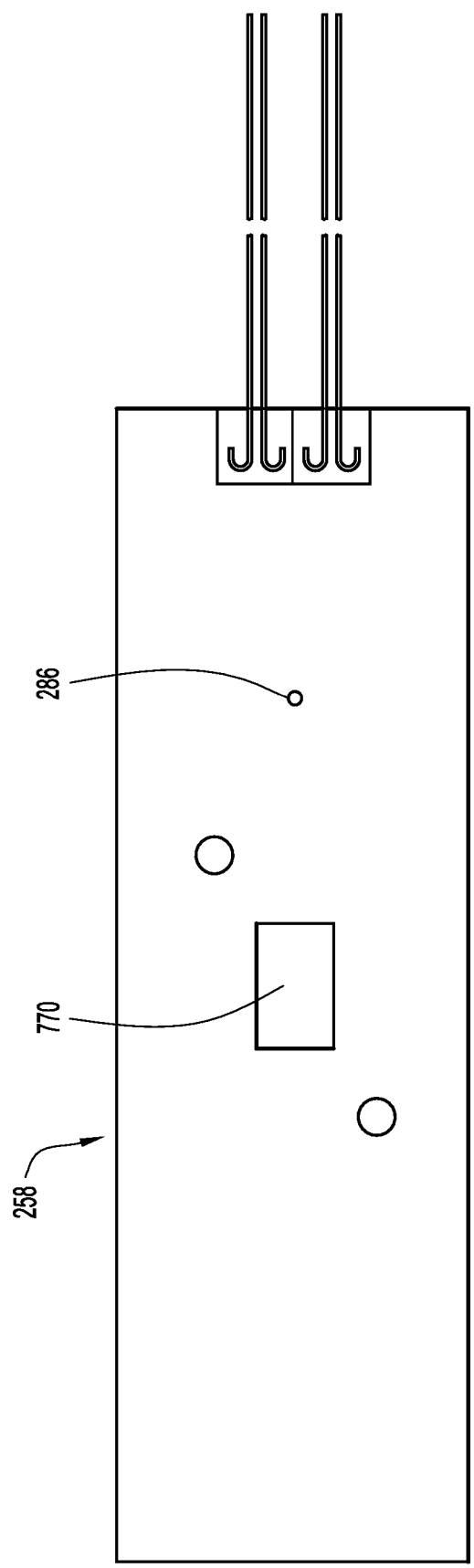
FIG. 7 is a view in elevation of a heating pad for a thermal treatment system heating assembly according to an embodiment of the present invention.

Heat control circuit 520 includes an assembly control unit 600 for each heating assembly of the control unit. Each assembly control unit 600 includes a heater controller 610 and heater 258. Heater controller 610 receives signals from system controller 510 and controls heater 258 accordingly. Referring to FIG. 7, heater 258 is preferably in the form of a generally rectangular silicon rubber heating pad that is adhered to bottom wall 252 of the heating plate. The heating pad includes a generally rectangular opening 770 defined therein to permit access through the opening and the heating plate to the medical item for temperature measurements by temperature sensors 272, 274. Further, temperature sensor 286 is disposed on heater 258 to measure excessive heater temperature.

Referring back to FIG. 6, each assembly control unit 600 further includes various connectors 630, 640, 650. Connector 630 enables communication between heater controller 610 and heater 258 to enable the heater controller to provide control signals to the heater. Connectors 640 of each assembly control unit are coupled together in a daisy chain type fashion to distribute power signals, while connectors 650 of each assembly control unit are coupled together in daisy chain type fashion to distribute signals from system controller 510. Connectors 650 further enable medical item temperature and detection information to be transmitted to system controller 510 from the coupled heating assemblies.

Figure 8:
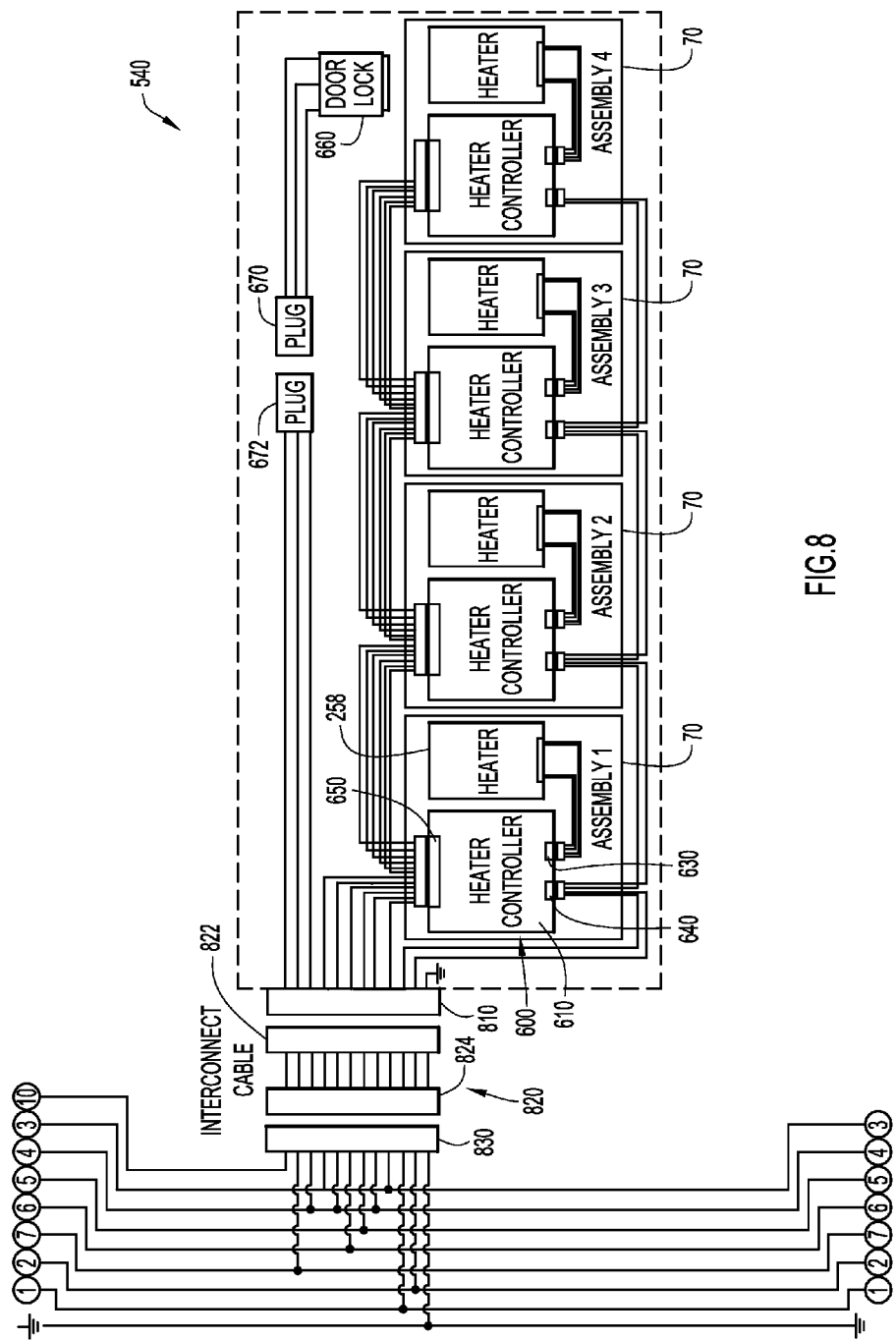
FIG. 8 is a schematic diagram of a heat control circuit of the control circuit of FIG. 5 for a modular unit according to an embodiment of the present invention.

An exemplary heat control circuit 540 for a modular unit 40 is illustrated in FIG. 8. Initially, heat control circuit 540 is substantially similar to heat control circuit 520 described above. In particular, heat control circuit 540 receives information from system controller 510 of control unit 20 to control corresponding heating assemblies 70 of a modular unit 40 (FIG. 1). In addition, modular unit 40 includes door lock 660 controlling actuation of door 55 and access to the heating assemblies as described above. The door lock is controlled by signals received from system controller 510 via plugs or connectors 670, 672 as described above. The signals are based on entry of a proper code to transition door 55 between open and closed states and control access to the medical items. One or more codes may be utilized to control the door lock (e.g., a code may be utilized to place the door in an open state for a predetermined time interval, a code may be utilized to lock the door while another code may be used to open the door, etc).

Heat control circuit 540 includes assembly control unit 600 for each heating assembly of the modular unit. Each assembly control unit 600 is substantially similar to the assembly control unit described above and includes heater controller 610 and heater 258. Heater controller 610 receives signals from system controller 510 and controls heater 258 as described above. In addition, each assembly control unit 600 includes various connectors 630, 640, 650 each as described above. Connector 630 enables communication between heater controller 610 and heater 258 to enable the heater controller to provide control signals to the heater. Connectors 640 of each assembly control unit are coupled together in a daisy chain type fashion to distribute power signals, while connectors 650 of each assembly control unit are coupled together in daisy chain type fashion to distribute signals from system controller 510. Connectors 650 further enable medical item temperature and detection information to be transmitted to system controller 510 from the coupled heating assemblies.

In addition, heat control circuit 540 includes a connector 820 to couple a connector 810 of the modular unit to a connector 830 transferring signals between the modular unit and control unit 20. Connectors 810, 830 are connected via an interconnect cable 820. The interconnect cable includes connectors 822, 82.4 at opposing ends to interface with connectors 810, 830 and couple the modular unit to the control unit to receive signals to control door lock 660 and heater 258, and provide medical item temperature and detection information to the control unit. Each modular unit 40 preferably includes a heat control circuit substantially similar to heat control circuit 540 described above.

An example heater controller 610 of heat control circuits 520, 540 according to an embodiment of the present invention is illustrated in FIG. 9. Specifically, heater controller 610 includes a processor 960, a relay 930, temperature sensors 272, 274, presence sensor 277, and a type circuit 970. Processor 960 is connected to temperature sensors 272, 274, relay 930, presence sensor 277, and type circuit 970. The processor controls heater 258 of a corresponding heating assembly based on a heater temperature measured by temperature sensor 286, medical item temperature measured by temperature sensors 272, 274, detection information produced by presence sensor 277, and a set point or desired temperature received from system controller 510. In addition, processor 960 provides medical item temperature and detection information to system controller 510 for control of display 60 and generation of reports.

Specifically, presence sensor 277 is connected to processor 960 and facilitates control of a corresponding heater and residence time measurement in accordance with the presence of a medical item (e.g., medical solution container, etc.) on a corresponding heating assembly. Presence sensor 277 includes an optical sensor 920 to receive infrared signals, and an infrared emitter 910. By way of example, the optical sensor may be implemented by a Si1102-A-GMR detector available from Silicon Labs. Processor 960 receives information from the optical sensor to determine the presence of the medical item (e.g., medical solution container, etc.) on the heating plate. In particular, when a medical item (e.g., medical solution container, etc.) is initially placed on a heating plate, infrared signals transmitted by emitter 910 are reflected back toward optical sensor 920. The optical sensor detects the reflected signals, and processor 960 senses this condition and commences measuring elapsed time for the medical item on the heating assembly. The processor may store the elapsed time in memory in order to recover and maintain the residence time measurement in the event of a power failure.

When the medical item is removed from the heating plate, the optical sensor detects weak or no reflected signals. Processor 960 detects this condition and resets the elapsed time. Further, the processor disables the corresponding heater. Thus, when the optical sensor indicates no medical item on a heating plate, the timer is reset and the corresponding heater is disabled.

Temperature sensor 286 resides on heater 258 as described above and is coupled to processor 960 via connector 630 (e.g., TRAY_PRIM as viewed in FIG. 9). The heater temperature facilitates disablement of the heater in response to detecting a heater temperature in excess of a predetermined threshold temperature (e.g., 150° F.) as described above. Basically, temperature sensor 286 of a heating assembly provides a temperature indication of the corresponding heater to processor 960. The processor disables the corresponding heater (e.g., disables power to the corresponding heater) in response to the measured temperature exceeding the predetermined threshold temperature. Temperature sensor 286 is preferably implemented by a thermistor or other resistance temperature detecting device. However, the temperature sensor may alternatively be implemented by any suitable temperature sensing device.

Type circuit 970 indicates the type of medical item. By way of example, the type circuit provides information indicating a one liter or three liter medical solution container. The type circuit includes jumper pins 972, where the settings of the jumper pins indicate the type of medical item. The type information is provided to processor 960 to control heater 258. For example, the indication of a three liter medical solution container generally requires greater heat from heater 258 to maintain the desired rapid heating times for this type of medical item (relative to the one liter medical solution containers).

Processor 960 may be implemented by any conventional or other controller, processor and/or circuitry. By way of example, the processor may be implemented by a PIC18F26J50I/ML processor available from Microchip Technology. The processor receives signals from temperature sensor 286 (indicating the heater temperature), temperature sensors 272, 274 (indicating the temperature of a medical item (e.g., medical solution container) in contact with the sensors (e.g., the medical solution container disposed on the heating plate surface)), optical sensor 920 of presence sensor 277 (indicating the presence of a medical item), and type circuit 970 (indicating the type of medical item). The temperature measurements from temperature sensors 272, 274 are compared, and an error condition is indicated when the temperature measurements deviate by more than a threshold amount (e.g. 0.5° F.). An error condition may further be indicated in response to the heater temperature being excessive (e.g., greater than 150° F.). In the case of an error condition or the absence of a medical item, heater 258 of the heating assembly is disabled.

If the medical item and heater temperature measurements are satisfactory (and the medical item is present), a medical item temperature is determined from an average of the temperature measurements from temperature sensors 272, 274. In response to the medical item temperature being equal to or exceeding a desired temperature entered by a user for that heating assembly, the processor generates signals to disable the corresponding heater (e.g., disable power to the corresponding heater). Conversely, when the medical item temperature is below the desired temperature, the controller generates signals to enable the corresponding heater (e.g., enable power to the corresponding heater). Temperature sensors 272, 274 are preferably implemented by thermistors or other resistance temperature detecting devices. However, the temperature sensors may alternatively be implemented by any suitable temperature sensing devices.

Processor 960 is coupled to relay 930 that provides signals from the processor to connectors 630, 640 for distribution among the heating assemblies of a control or modular unit as described above. The relay may be implemented by any conventional or other device for conveying signals (e.g., relay, bus, wires, amplifier, etc.). Further, the processor is coupled to connector 650 for distribution of signals among the heating assemblies of a control or modular unit as described above. In addition, processor 960 transfers the residence time, medical item temperature, excessive temperature detections, and medical item presence information for the corresponding heating assembly to system controller 510 via connector 650 for display on display 60 and generation of reports as described above. In addition, the display indicates the status of the medical item temperature in relation to the set point or desired temperature as described above (e.g., in the form of color-coded bars or objects). This information may be transmitted at any desired intervals for display by the system controller. The use of a processor 960 within each heating assembly decreases response time and provides enhanced control of heater 258 for heating medical items to desired temperatures.

Referring to FIG. 10, system controller 510 provides various information on display 60. For example, the display provides the current date, time, and set point temperature (e.g., "SET PT" as viewed in FIG. 10), and for each heating assembly of the control and modular units (e.g., labeled 1-16 as viewed in FIG. 10), the medical item temperature and current residence time of the medical item placed on that heating assembly. The display further provides a visual indication for a heating assembly when excessive temperatures have, been detected for that heating assembly (e.g., an over temperature (e.g., an "OVER TEMP") indication) or when a medical item is not present on that heating assembly (e.g., an "EMPTY" or "RELOAD" indication) or recently inserted (e.g., a "PRE WARMING" indication).

Moreover, the display indicates when a medical item on a heating assembly has attained or is near (e.g., within a predetermined or user-specified range from) the desired or set point temperature. The indicator is preferably in the form of a colored bar or other object to indicate when the medical item temperature is below (e.g., a blue bar or object indicating the medical item is being warmed), at or near (a green bar or object indicating that the medical item temperature is at or within a desired range from), or exceeds (e.g., a red bar or object indicating that the medical item temperature is beyond a desired range (an over temperature condition) from) the desired temperature as described above.

In addition, various system settings may be adjusted by a user via display 60 and/or input devices 576. The settings may be accessed via an icon 1002 on display 60 (e.g., "Settings" as viewed in FIG. 10), or actuation of input devices 576. The adjustable settings include a time zone, set point temperature, data logging intervals, and units for temperature (e.g., Celsius, Fahrenheit, etc.).

In addition, system controller 510 may generate a report indicating heating of the medical items as illustrated, by way of example, in FIG. 11. In particular, the report includes general information (e.g., company, warmer model and serial number, temperature scale, date, etc.), summary information (e.g., number of warning messages, maximum item temperature, minimum item temperature, number of items exceeding a threshold temperature, maximum number of days of warming, number of items warmed, etc.). Further, the report includes a table of measurement readings, where each reading indicates, by way of example, the date and time, set point temperature, the temperature measurements from each of the heating assemblies, and warnings.

The generated report is downloaded from system controller 510 onto a removable storage device (e.g., Universal Serial Bus (USE) or other drive, etc) for viewing on a computer system or processing device. The removable storage device may interface the control unit via port 39 on control panel 37 as described above. The download may be initiated by actuation of an icon 1004 on display 60 (e.g., "Report" as viewed in FIG. 10), or via input devices 576 of control unit 20. The report is preferably generated as a comma-separated values (CSV) file, but may be generated in any desired format or arrangement. The generated file may be viewed via various word processing, spreadsheet, or other applications. The information may be removed from the system once the report is downloaded in order to conserve memory.

Operation of system 100 is described with reference to FIGS. 1-11. Specifically, a user selects one or more medical items (e.g., medical solution bags or bottles containing saline or IV solutions, antibiotics or other drags, blood, etc.) for heating by the system, and determines the appropriate temperature for the medical item. The system may be transported to a desired site, and include control unit 20 with one or more modular units 40. The user subsequently activates power switches 515, 525, and opens doors 35, 55 of the control and/or modular units. The selected medical items (e.g., medical solution containers, etc.) are placed into the control and/or modular units on any desired heating assemblies.

Doors 35, 55 are subsequently pivoted to a closed state and desired temperatures for the selected medical items are entered into the system via display 60 and/or input devices 576 as described above, where the medical items may individually be heated by the heating assemblies to the same temperatures. The system controller transmits the set point temperature and other information to heat control circuits 520, 540 to control heating and measurement of residence time. The medical items within the system may be viewed through the doors. In response to placement of a medical item on a heating plate bottom wall, the medical item engages corresponding temperature sensors 272, 274 and causes detection of infrared signals by presence sensor 277. The reflected infrared signals are detected by a corresponding heat control circuit that initiates measurement of residence or elapsed time. The heat control circuit controls the corresponding heater (e.g., enables or disables the heater) in accordance with signals from corresponding temperature sensors 272, 274, 286, presence sensor 277, and type circuit 970 as described above. The heater applies heat to the corresponding heating plate bottom wall, while the heating plate side walls conduct heat from the bottom wall to evenly distribute heat to the medical item. Disablement of the heater occurs in response to excessive heater temperature, the absence of a medical item, or erroneous temperature measurements by temperature sensors 272, 274 as described above.

Heat control circuits 520, 540 transfer the residence time, medical item temperature, excessive temperature detection, medical item presence, and other information for the heating assemblies to system controller 510 for display on display 60. The display provides a status of medical item heating based on color-coded objects as described above.

In response to attaining the desired temperature, the medical item is removed from a heating plate via door 35, 55. The corresponding presence sensor detects the absence of (or weak) reflected infrared signals, thereby enabling resetting of the residence or elapsed time, disabling of the corresponding heater, and enabling display of a reload or empty indicator for that heating assembly. Further, a user may download a report including various temperature and other information to a removable storage device as described above. A new medical item may be placed on that heating plate, where the presence sensor indicates the presence of that medical item, thereby initiating residence time measurement and display of information to repeat the process for this medical item. The above process may be repeated for additional medical items. A user may utilize any quantity or combination of heating assemblies in any fashion (e.g., within the same or different unit) to heat medical items within the system.

It will be appreciated that the embodiments described above and illustrated in the drawings represent only a few of the many ways of implementing embodiments for warming a plurality of medical items to desired temperatures.

The housings of the control and modular units (e.g., panels, walls, etc.) may be of any size, shape or configuration and may be constructed of any suitable materials including, but not limited to, electrogalvanized steel. The housing components may be connected via any conventional fastening techniques (e.g., welding, nuts and bolts, etc.). Any portion of the housings may be constructed of a transparent material. The heating assemblies may be of any quantity, shape or size and may hold any quantity of medical solution containers or other items (e.g., one or more containers or items). The doors may be of any quantity, shape or size, may be constructed of any suitable materials, and may be connected to the housings at any suitable locations in any fashion to pivot in any desired direction and/or manner (e.g. hinged doors, sliding doors, removable panel doors, etc.). Further, the doors may include a window of any size or shape, while the doors and/or window may be constructed of any translucent, transparent or other materials. The doors may include any quantity of any type of handle or latching mechanism disposed at any suitable locations.

The control and modular units may warm any quantity of any type of medical solution container or other item to any desired temperature. The system controller and processors of the control and modular units may be implemented by any conventional or other microprocessor or controller. Software for the controller and processors may be implemented in any desired computer language and could be developed by one of ordinary skill in the computer arts based on the functional descriptions contained herein. The controller and processors may alternatively be implemented by any type of hardware, software and/or other processing circuitry, and may be available pre-programmed for immediate use. The various functions of the controller and processors may be distributed in any manner among any quantity of software modules, processors and/or circuitry. The algorithms and/or processes described above may be modified in any manner that accomplishes the functions described herein.

The controller and processors may be disposed on or within the control and modular units at any suitable locations. The controller and processors may control the heater to any desired temperature. The control unit may include any quantity of any type of input device (e.g., keys, buttons, mouse, voice, touch screen, etc.) to facilitate entry of any desired temperatures or any other information. The system controller may include or control any quantity of any type of display of any shape or size to convey any desired information. The display may be integral with or detached from the system controller, control unit or modular unit, and may include an LED, LCD or monitor type display, indicator lights, or any other mechanism for indicating desired and/or measured temperature or any other information. Further, the display may include any type of buttons or data entry devices to program the system controller in any manner. The processors may employ any conventional or other control algorithms (e.g., fuzzy logic, PID, etc.). The system may include any quantity of system controllers or processors to accommodate any quantity of heating assemblies, or a single system controller and/or a single processor may accommodate plural heating assemblies.

The heating plate may be of any quantity, shape, size or configuration to heat a medical solution or other item. The heating plate may include any quantity of conducting and/or non-conducting walls of any shape or size and may be constructed of any suitable materials. The heater may be implemented by any quantity of any conventional heater or other heating device (e.g., conduction, convection, microwave or other radiation, etc.). The heating plate may include any quantity of heaters of any shape or size arranged in any configuration (e.g., strips, annular, segments, etc.) and disposed at any suitable locations for applying heat. The heater may be attached to the heating plate via any conventional or other fastening technique (e.g., pressure sensitive or other adhesives, etc.). The system may alternatively include any quantity of heaters of any shape or size disposed at any suitable locations on the heating plate or within the system. The heater and heating plate may include any quantity of openings of any shape or size, and defined at any suitable locations.

The temperature sensors may be implemented by any quantity of any type of conventional or other temperature measuring devices (e.g., RTD, infrared, etc.) and may be disposed at any suitable locations on the heating assembly or heater. Alternatively, a single temperature sensor may be employed to facilitate control of the heater in response to measured medical item and excessive heater temperatures. The medical item temperature may be derived from any quantity of temperature sensors (e.g., one or more, etc.) disposed at any locations relative to the medical item, where the individual temperature measurements may be combined in any fashion (e.g., averaged, selection of one of the temperatures, etc.). The error condition may be indicated in response to any desired deviation between temperature sensors. Further, the overtemperature and excessive temperature conditions may be indicated based on any desired temperature thresholds.

The presence sensor may be implemented by any quantity of any type of pressure or other switch, or sensor (e.g., infrared, etc.) for detecting the presence of a medical solution container or other item. The presence sensor may be positioned at any location proximate the heating plate or within the systems to detect the presence of a medical solution container or other item.

The control and heat control circuits may utilize any conventional or other connectors or wiring to transfer power and other signals to system components. Further, the components of these circuits (e.g., power switch, relay, fuses, controllers, boards, power sources, connectors, processors, etc) may be implemented by any quantity of any conventional or other electrical components arranged in any fashion and performing the functions described above. The circuits may be disposed at any location on or within the housings and may be arranged in any fashion. The fuses may be implemented by any conventional or other fuses or limiting devices configured for any desired current level. The power switch, display, and input devices may be disposed at any suitable locations on or within the housings.

The systems may be used at any suitable locations (e.g., hospital or other medical facility, emergency medical or other vehicles, etc.) with any types of power sources (e.g., AC, DC, wall outlet jack, batteries, vehicle power system, etc.) to heat any quantity of any type of medical solution container or other item. The systems preferably heat items to desired temperatures within the approximate range of 32° F.-104° F., but may be utilized to heat the items to any desired temperatures or temperature ranges.

The control and modular units may be mounted on or supported by any type of support structure (e.g., wall, cart, table, floor, stand, etc.). The platform and pedestal may be of any type, shape or size, may be constructed of any suitable materials. The platform may include any quantity of any type of wheels or rollers disposed at any suitable locations to facilitate transport of the system. The control and modular units may be arranged in any fashion, and communicate via any suitable media (e.g., wired, wireless, networks (e.g., local area and/or wide area networks, Internet, etc.), etc.).

The residence time may be initiated by the processor and/or manually by a user via control or input devices (e.g., keys, buttons, etc.) to initiate time measurement. The time may be incremented or decremented to measure elapsed time and may be measured and/or displayed in any desired format or time units (e.g., hours, minutes, seconds, etc.). The system may further include visual or audio alarms to notify a user when a particular time interval expired, or disable heating upon expiration of that time interval. The system may measure and/or display various time intervals (e.g., measure residence time within the system, measure residence time on heating plate, etc.).

The relay may be implemented by any conventional or other relays or circuitry. The relay may provide any signals to the connectors. The power sources may be implemented by any conventional or other power sources or circuitry and may provide any desired power signal (e.g., 12V DC, AC, voltage, current, etc.).

The heating assemblies may be of any quantity, shape or size, and may be constructed of any suitable materials. The heating assemblies may be oriented at any desired angle and may be mounted within the cabinet or other structure in any desired fashion via any conventional or other mounting mechanisms (e.g., rails, brackets, ledges, etc.). The control and modular units may include any quantity of heating assemblies.

The system controller may directly control any quantity of heating assemblies. The system controller may further communicate in any fashion with the heat control circuits via any suitable protocols. The system controller may receive any desired information from a user, transfer any desired information to the heat control circuits and may utilize any quantity of any type of indicators (e.g., visual, audio, LEDs, display, etc.) to indicate system conditions (e.g., power on, attainment of set point temperature, etc.).

The display and report may provide any information arranged in any fashion. The heating assemblies may include any identifiers (e.g., symbols, characters, numbers, etc) to associate a heating assembly with displayed information, and may utilize any symbols or object of any desired shapes, sizes or colors to indicate the medical item temperature in relation to a desired or set point temperature. The various status conditions relative to the set point temperature (e.g., below, at or above the set point temperature) may be defined to reside within any desired ranges from the set point temperature. The report may be downloaded, retrieved and otherwise accessible from the control unit and/or modular units via any suitable techniques (e.g., memory device and/or port, networks (e.g., local area and/or wide area networks, Internet, etc.), etc.).

The heat control circuits may control any quantity of heating assemblies and may transfer and receive any desired information from the system controller. The heat control circuits may store residence time or any other information (e.g., temperature, etc.) in memory in order to recover and maintain residence time measurements and/or heating in the event of a power failure or other interruption of power (e.g., power off, etc.). The heat control circuits may further detect the temperature of a newly placed item prior to commencing heating. If the item has a temperature above a threshold indicating the item has been previously warmed, heating may be disabled and/or a user may be notified of the prior warming and/or that the residence time does not include the prior warming. The heat control circuits may detect any conditions and provide the information to the system controller. The heat control circuits may communicate with the system controller synchronously or asynchronously and at any desired time or time intervals. The functions of the system controller and heat control circuits may be distributed in any fashion among the controller and heat control circuits (e.g., the system may operate without the controller or heat control circuits). The heating assemblies may be individually controlled to heat corresponding medical items to the same or different desired temperatures.

The door locks may be implemented by any conventional or other locks, and be actuated by any suitable mechanisms (e.g., mechanical or electronic key, biometrics, codes of any length and including any types of symbols or characters, etc.). The door locks may be actuated from the control unit and/or from any of the modular units.

The present invention embodiments are not limited to the specific medical items described above, but may be utilized with any medical items to selectively thermally treat (e.g., heat and/or cool) the medical items to desired temperatures (e.g., user specified, predetermined, etc.).

From the foregoing description, it will be appreciated that the invention makes available a novel plural medical item warming system and method for warming a plurality of medical items to desired temperatures, wherein a thermal treatment system includes a modular configuration with a control unit and one or more modular units coupled to the control unit to thermally treat a plurality of medical items.

Having described preferred embodiments of a new and improved plural medical item warming system and method for warming a plurality of medical items to desired temperatures, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A temperature control system for thermally treating medical items to desired temperatures comprising:
  one or more modular units each including a first housing containing at least one first thermal treatment assembly to thermally treat a corresponding first medical item; and
  a control unit coupled to each of the one or more modular units and including:
    a second housing containing at least one second thermal treatment assembly to thermally treat a corresponding second medical item; and
    a controller to facilitate entry of a desired temperature for each said first and second medical item within said control unit and said one or more modular units, to control heating by said control unit and said one or more modular units based on said desired temperature, and to display information pertaining to the heating by said control unit and said one or more modular units;
  wherein each said first thermal treatment assembly detects a type of the corresponding first medical item and controls an amount of heat applied to the corresponding first medical item based on the detected type of the corresponding first medical item to maintain consistent heating times for attaining said desired temperature between different types of the corresponding first medical item; and
  wherein each said second thermal treatment assembly detects a type of the corresponding second medical item and controls an amount of heat applied to the corresponding second medical item based on the detected type of the corresponding second medical item to maintain consistent heating times for attaining said desired temperature between different types of the corresponding second medical item.

2. The temperature control system of claim 1, wherein each said first and second thermal treatment assembly includes:
  a timer to measure residence time.

3. The temperature control system of claim 1, wherein each said first and second thermal treatment assembly includes:
  a sensing device to detect the presence of the corresponding first and second medical item and to enable thermal treatment in response to said detection.

4. The temperature control system of claim 3, wherein said sensing device includes an IR emitter and an optical sensor.

5. The temperature control system of claim 1, wherein said control unit displays for each said first and second thermal treatment assembly at least one of a residence time for the corresponding first and second medical item, temperature information for said corresponding first and second medical item, an indication of the absence of the corresponding first and second medical item, a first indication of a temperature within a predetermined range of the desired temperature, and a second indication of a temperature outside the predetermined range of the desired temperature.

6. The temperature control system of claim 5, wherein said first and second indications of temperature are color-coded.

7. The temperature control system of claim 1, wherein at least one of the first and second thermal treatment assemblies includes:
   a heating plate to distribute heat, wherein said heating plate includes at least one primary conducting section and at least one secondary conducting section; and
   a heater affixed and applying heat to said heating plate, wherein said heater is attached to and covers selected portions of said at least one primary conducting section to directly apply heat to said selected portions, wherein each said secondary conducting section is coupled to said at least one primary conducting section receiving said heater and receives said applied heat through conduction.

8. The temperature control system of claim 1, wherein said control unit generates a report with information pertaining to at least one of medical item information, temperature information for at least one of the first and second medical items, and warning messages.

9. The temperature control system of claim 8, wherein said control unit communicates said report electronically to an external device.

10. The temperature control system of claim 1, wherein said control unit communicates with each of said one or more modular units via a communication medium.

11. The temperature control system of claim 10, wherein said communication medium includes a wireless communication medium.

12. The temperature control system of claim 10, wherein said control unit is remote from at least one modular unit of the one or more modular units, and said communication medium includes a network.

13. The temperature control system of claim 1, further including:
   a support to support said control unit and said one or more modular units, wherein said support includes one of a cabinet, a pedestal, a table, a counter, and a recess in a wall.

14. The temperature control system of claim 13, wherein said support includes said cabinet, and said cabinet includes a plurality of rollers to transport said temperature control system.

15. A method of thermally treating medical items to desired temperatures within a temperature control system including a control unit coupled to one or more modular units, said method comprising:
   (a) receiving the medical items in said one or more modular units and said control unit, wherein said one or more modular units each include a first housing containing at least one first thermal treatment assembly to thermally treat a corresponding first medical item, wherein said control unit includes a second housing containing at least one second thermal treatment assembly to thermally treat a corresponding second medical item, and wherein said control unit is coupled to each of said one or more modular units;
   (b) facilitating entry of a desired temperature for each said first and second medical item within said control unit and said one or more modular units via said control unit and controlling heating by said control unit and said one or more modular units based on said desired temperature, wherein controlling heating includes:
      detecting, via each said first thermal treatment assembly, a type of the corresponding first medical item and controlling an amount of heat applied to the corresponding first medical item based on the detected type of the corresponding first medical item to maintain consistent heating times for attaining said desired temperature between different types of the corresponding first medical item; and
      detecting, via each said second thermal treatment assembly, a type of the corresponding second medical item and controlling an amount of heat applied to the corresponding second medical item based on the detected type of the corresponding second medical item to maintain consistent heating times for attaining said desired temperature between different types of the corresponding second medical item; and
   (c) displaying information, via said control unit, pertaining to the heating by said control unit and said one or more modular units.

16. The method of claim 15, wherein step (a) further includes:
   (a.1) measuring residence time.

17. The method of claim 15, wherein step (a) further includes:
   (a.1) detecting the presence of the corresponding first and second medical item and enabling thermal treatment in response to said detection.

18. The method claim 15, wherein step (c) further includes:
   (c.1) displaying for each said first and second thermal treatment assembly at least one of residence time for the corresponding first and second medical item, temperature information for said corresponding first and second medical item, an indication of the absence of the corresponding first and second medical item, a first indication of a temperature within a predetermined range of the desired temperature, and a second indication of a temperature outside the predetermined range of the desired temperature.

19. The method of claim 18, wherein step (c.1) further includes:
   (c.1.1) color coding said first and second indications of temperature.

20. The method of claim 15, wherein step (a) further includes:
   (a.1) applying heat to a heating plate of at least one of the first and second thermal treatment assemblies via a heater to distribute heat, wherein said heating plate includes at least one primary conducting section and at least one secondary conducting section and said heater is attached to and covers selected portions of said at least one primary conducting section to directly apply heat to said selected portions, and wherein each said secondary conducting section is coupled to said at least one primary conducting section receiving said heater and receives said applied heat through conduction.

21. The method of claim 15, wherein step (c) further includes:
   (c.1) generating a report with information pertaining to at least one of medical item information, temperature information for at least one of the first and second medical items, and warning messages.

22. The method of claim 21, wherein step (c) further includes:

(c.1.1) communicating said report electronically to an external device.

23. The method of claim 15, further comprising:
enabling communications between said control unit and each of said one or more modular units via a communication medium.

24. The method of claim 23, wherein said communication medium includes a wireless communication medium.

25. The method of claim 23, wherein said control unit is remote from at least one modular unit of the one or more modular units, and said communication medium includes a network.

26. The method of claim 15, further comprising:
supporting said control unit and said one or more modular units via one of a cabinet, a pedestal, a table, a counter, and a recess in a wall.

27. The method of claim 26, wherein said control unit and said one or more modular units are supported via said cabinet, wherein said cabinet includes a plurality of rollers, and said method further includes:
transporting said temperature control system via said cabinet with said plurality of rollers.

\* \* \* \* \*